US011214602B2

(12) United States Patent
Nunn

(10) Patent No.: US 11,214,602 B2
(45) Date of Patent: Jan. 4, 2022

(54) COVERSIN VARIANTS LACKING C5 BINDING

(71) Applicant: VOLUTION IMMUNO PHARMACEUTICALS SA, Geneva (CH)

(72) Inventor: Miles Andrew Nunn, Geneva (CH)

(73) Assignee: Volution Immuno Pharmaceuticals, SA, Geneva (CH)

( * ) Notice: Subject to any disclaimer, the term of this patent is extended or adjusted under 35 U.S.C. 154(b) by 0 days.

(21) Appl. No.: 16/603,357

(22) PCT Filed: Apr. 20, 2018

(86) PCT No.: PCT/EP2018/060240
§ 371 (c)(1),
(2) Date: Oct. 7, 2019

(87) PCT Pub. No.: WO2018/193121
PCT Pub. Date: Oct. 25, 2018

(65) Prior Publication Data

US 2020/0385434 A1 Dec. 10, 2020

(30) Foreign Application Priority Data

Apr. 21, 2017 (GB) ...................................... 1706406

(51) Int. Cl.
*C07K 14/435* (2006.01)
*A61K 38/00* (2006.01)

(52) U.S. Cl.
CPC ........ *C07K 14/43527* (2013.01); *A61K 38/00* (2013.01)

(58) Field of Classification Search
None
See application file for complete search history.

(56) References Cited

U.S. PATENT DOCUMENTS

2006/0058228 A1* 3/2006 Kelly ............... G01N 33/57419 530/317
2020/0113971 A1 4/2020 Nunn et al.
2020/0385434 A1 12/2020 Nunn
2021/0113658 A1 4/2021 Weston-Davies

FOREIGN PATENT DOCUMENTS

| | | | |
|---|---|---|---|
| EP | 1739078 | A1 | 1/2007 |
| WO | 2004106369 | A2 | 12/2004 |
| WO | 2007028968 | A1 | 3/2007 |
| WO | 2008113834 | A2 | 9/2008 |
| WO | 2009098454 | A2 | 8/2009 |
| WO | 2009098454 | A3 | 6/2010 |
| WO | 2010100396 | A1 | 9/2010 |
| WO | 2012178083 | A1 | 12/2012 |
| WO | 2015185945 | A2 | 12/2015 |
| WO | 2016198133 | A1 | 12/2016 |
| WO | 2018193120 | A1 | 10/2018 |

OTHER PUBLICATIONS

Peelle, Beau R. et al.; "Probing the interface between biomolecules and inorganic materials using yeast surface display and genetic engineering." Acta Biomaterialia (2005) 1 p. 145-154.*
Bogan, Andre A. and Thorn, Kurt S.; "Anatomy of hot spots in protein interfaces." J. Mol. Bil. (1998) 280 p. 1-9.*
Nunn et al., "Therapeutic Development of Complement C5 Inhibitor Coversin (TM) with Extended Half-Life Via PASylation (R)," Biosis, Biosciences Information Service, Philadelphia, PA,US, Dec. 2, 2016 (2 pages).
Kuhn et al., "PASylated Coversin, a C5-Specific Complement Inhibitor with Extended Pharmacokinetics, Shows Enhanced Anti-Hemolytic Activity in Vitro," Bioconjugate Chemistry, vol. 27, No. 10, Sep. 26, 2016, pp. 2359-2371, XP055646970 (13 pages).
Yokomizo et al., "Hydroxyeicosanoids bind to and activate the low affinity leukotriene B4 receptor BLT2," J. Biol. Chem. 276, 12454-12459 (2001).
Ausubel et al., "Identification of signal transduction pathways leading to the expression of *Arabidopsis thaliana* defense genes," Advances in Molecular Genetics of Plant-Microbe Interactions vol. 1, pp. 357-364 (1991).
Barratt-Due et al., "Ornithodoros moubata complement inhibitor is an equally effective CS inhibitor in pigs and humans", J Immunol. 187(9):4913-9 (2011).
Bisgaard et al., "Bronchial hyperreactivity to leukotriene D4 and histamine in exogenous asthma," Br Med J. 290, pp. 1468-1471 (1985).
Breustedt et al., "Comparative ligand-binding analysis of ten human lipocalins," Biochim Biophys Acta 1764(2) pp. 161-173 (2006).
Chen et al., "Neutrophil derived leukotriene B4 is required for inflammatory arthritis," J. Exp. Med. 203, pp. 837-842 (2006).
Curry et al.. "Nonsteroidal Antiinflammatory Drugs: A Review," Journal of the American Animal Hospital Association 41, 298-309 (2005).
Czarnetzki, "Increased monocyte chemotaxis towards leukotriene B4 and platelet activating factor in patients with inflammatory dermatoses," Clin Exp Immunol. 54, pp. 486-492 (1983).
Del Prete et al., "Regulation of dendritic cell migration and adaptive immune response by leukotriene B4 receptors: a role for LTB4 in up-regulation of CCR7 expression and function," Blood, 109, 626-631 (2007).
Drazen J. M., "Comparative contractile responses to sulfidopeptide leukotrienes in normal and asthmatic human subjects," Ann NY Acad Sci. 524, 289-297 (1988).

(Continued)

*Primary Examiner* — Fred H Reynolds
(74) *Attorney, Agent, or Firm* — McNeill Baur PLLC

(57) ABSTRACT

The invention is directed to modified Coversin polypeptides which exhibit leukotriene or hydroxyeicosanoid binding activity and reduced or absent C5 binding relative to the unmodified Coversin polypeptide; to nucleic acid molecules encoding said modified Coversin polypeptides; vectors and host cells comprising said nucleic acid molecules; and methods of treating or preventing diseases or conditions mediated by a leukotriene or hydroxyeicosanoid in a subject comprising administering said modified polypeptides or nucleic acids to a subject.

48 Claims, 14 Drawing Sheets

Specification includes a Sequence Listing.

(56) References Cited

OTHER PUBLICATIONS

Dube et al., Zileuton: the first leukotriene inhibitor for use in the management of chronic asthma. In: Drazen JM, Dahlen S, Lee TH, eds. Five-lipoxygenase Products in Asthma, pp. 391-428 (1998).
Ford-Hutchinson, A. (1990). Leukotriene B4 in inflammation. Crit. Rev. Immunol. 10, 1-12.
Giclas, P. C, "alternative pathway evaluation," sections 13.1, Current Protocols in Immunology, vol. 3, Complement, 9 pages (1994).
Giclas, P. C, "Classical pathway evaluation," sections 13.2, Current Protocols in Immunology, vol. 3, Complement, 26 pages (1994).
Gregory et al.,"Inhaled house dust mite induces pulmonary T helper 2 cytokine production," Clin Exp Allergy, 39(10): p. 1597-1610 (2009).
Hao and Breyer, "Physiologic and pathophysiologic roles of lipid mediators in the kidney," Kidney International 71, pp. 1105-1115(2007).
Harrison and Murphy, "Isoleukotrienes are biologically active free radical products of lipid peroxidation," J. Biol. Chem. 270, pp. 17273-17276 (1995).
Hepburn et al., "In vivo characterisation and therapeutic efficacy of CS-specific inhibitor from the soft tick Ornithodoros moubata," J Biol Chem. 282, 8292-8299 (2007).
Hoover et al., "Leukotriene B4 action on endothelium mediates augmented neutrophil/endothelial adhesion," Proc. Nat. Acad. Sci. U.S.A. 81, 2191-2193 (1984).
Imig, J.D., "Eicosanoid regulation of the renal vasculature," Am. J. Physiol. Renal Physiol. 279, pp. F965-F981 (2000).
Jore et al., "Structural basis for therapeutic inhibition of complement CS," Nature Structural & Molecular Biology 23, pp. 378-386 (2016).
Kim et al., "A unique requirement for the leukotriene B4 receptor BLT1 for neutrophil recruitment in inflammatory arthritis," J. Exp. Med. 203, pp. 829-835 (2006).
Kim et al., "Regulation of immune cells by eicosanoid receptors," The Scientific World Journal 7, pp. 1307-1328 (2007).
Klaas et al., "Neutrophils mediate immune modulation of dendritic cells through glycosylation-dependent interactions between Mac-1 and DC-SIGN," J. Exp. Med. 201, pp. 1281-1292 (2005).
Lundeen et al., "Leukotriene B4 receptors BLT1 and BLT2: expression and function in human and murine mast cells," J. Immunol. 177, pp. 3439-3447 (2006).
Mans B J et al., "Function, mechanism and evolution of the moubatin-clade of soft tick lipocalins", Insect Biochem Mol Biol., 38(9): 841-852 (Sep. 2008).
Miyahara et al. "Role of the LTB4/BLT1 Pathway in Allergen-induced Airway Hyperresponsiveness and Inflammation," Allergol Int. 55, 91-7 (2006).
Myszka D.G., "Improving biosensor analysis," J Mol Recognit. 12(5):279-284 (1999).
Noiri et al., "An in vivo approach showing the chemotactic activity of leukotriene 8(4) in acute renal ischaemic-reperfusion injury," Proc Nat Acad Sci USA 97, pp. 823-828 (2000).
Nunn et al., "Complement inhibitor of CS activation from the soft tick Omithodoros moubata," J. Immunol. 174, pp. 2084-2091 (2005).
Nunn et al., "Therapeutic Development of Complement C5 Inhibitor Coversin (TM) with Extended Half-Life Via PASylation (R)" Database accession No. PREV201700342092, abstract & Blood, vol. 128, No. 22, Dec. 2, 2016, p. 5900, 58th Annual Meeting and Exposition of the American-Society-of-Hematology; San Diego, CA, USA, (Dec. 3-6, 2016).
Paesen et al., "Tick histamine-binding proteins: isolation, cloning, and three-dimensional structure," Mol Cell 3, pp. 661-671 (1999).
Peters-Golden and Henderson, "Leukotrienes," N. Eng. J. Med. 357, pp. 1841-1854 (Nov. 1, 2007).
Powell and Rokach, "Biochemistry, biology and chemistry of the 5-lipoxygenase product 5-oxo-ETE," Prag Lipid Res. 44, pp. 154-183 (2005).
Roversi et al., "Bifunctional Lipocalin Ameliorates Murine Immune Complex-induced Acute Lung Injury," J. Biol. Chem 288: pp. 18789-18802 (2013).
Roversi et al., "The structure of OmCI a novel lipocalin inhibitor of the complement system," J. Mal. Biol. 369, pp. 784-793 (2007).
Samuelsson, B. "Leukotrienes: mediators of immediate hypersensitivity reactions and inflammation," Science 220, pp. 569-575 (1983).
Schlapschy et al., "PASylation: a biological alternative to PEGylation for extending the plasma half-life of pharmaceutically active proteins," Protein Eng Des Sel 26: pp. 489-501 (2013).
Schleuber and Skerra, "Tuning ligand affinity, specificity, and folding stability of an engineered lipocalin variant—a so-called 'anticalin'—using a molecular random approach," Biophys Chem. 96(2-3) pp. 213-228 (2002).
Schwartz et al., "Phase I and Pharmacokinetic Study of LY293111, an Orally Bioavailable LTB4 Receptor Antagonist, in Patients With Advanced Solid Tumors," Journal of Clinical Oncology, 23, pp. 5365-5373 (2005).
Sebaldt et al., "Inhibition of eicosanoid biosynthesis by glucocorticoids in humans," Proc Natl Acad Sd. U.S.A. 8, pp. 6974-6978 (1990).
Shao et al., "Targeted Disruption of Leukotriene B4 Receptors BLT1 and BLT2: A Critical Role for BLTI in Collagen-Induced Arthritis in Mice," J. Immunol. 176, pp. 6254-6261 (2006).
Sharma, J.N. and Mohammed, L.A, "The role of leukotrienes in the pathophysiology of inflammatory disorders: is there a case for revisiting leukotrienes as therapeutic targets?" Immunopharmacology 14, pp. 10-16 (2006).
Showell et al., "The in vitro and in vivo pharmacologic activity of the potent and selective leukotriene B4 receptor antagonist CP-105696," J. Pharm. Exp. Ther. 273, 176-184 (1995).
Sitaru, C., et al. Induction of dermal-epidermal separation in mice by passive transfer of antibodies specific to type VII collagen J Clin Invest 2005;115:870-8.
Tager and Luster, "BLT1 and BLT2: the leukotriene 8(4) receptors." Prostaglandins Leukot. Essent. Fatty Acids 69, pp. 123-134 (2003).
Taube et al. "The leukotriene B4 receptor BLT1 is required for effector C08+ T cell-mediated, mast cell-dependent airway hyperresponsiveness," J. Immunol. 176, pp. 3157-3164 (2006).
Yamaoka et al., "Leukotriene B4 enhances activation, proliferation, and differentiation of human B lymphocytes," J. Immunol. 143, pp. 1996-2000 (1989).
Yokomizo et al., "AG-protein coupled receptor for leukotriene B4 that mediates chemotaxis," Nature 387, pp. 620-624 (1997).
Yokomizo et al., "A second leukotriene 8(4) receptor, BLT2. A new therapeutic target in inflammation and immunological disorders," J. Exp. Med. 192, pp. 421-432 (2000).
Ihara et al., "Blockade of leukotriene B4 signalling pathway directly inhibits cell proliferation and induces apoptosis colon cancer," J Pharmacol Sci, pp. 1-9 (2006).
Anonymous, "Akari Therapeutics Announces Completion of Phase II COBALT Trial of Coversin in Patients with PNH and Further Progress of Clinical Trials—Akari Therapeutics," Feb. 6, 2016, 6 pages. Retrieved from the internet on Jun. 6, 2018: https://www.akaritx.com/2018/02/06/akari-therapeutics-announces-completion-phase-ii-cobalt-trial-coversin-patients-pnh-progress-clinical-trials/.
Anonymous, Atopic Keratoconjunctivitis Management: Diagnosis and Management, Aug. 1, 2016 (15 pages). Retrieved on Jun. 17, 2021: https://www.aimu.us/2016/08/01/atopic-keratoconjunctivitis-diagnosis-and-management/.
Anonymous, "TSGP2," Database UniProt [Online], Database Accession No. Q8I9U1, Oct. 5, 2016, 1 page.
Calder et al., "Experimental immune-meditated conjunctivitis (EIC): downregulation by Coversin, a dual C5 and LTB4 inhibitor," Annual Meeting of the Association for Research in Vision and Opthamology, vol. 59, May 3, 2018, p. 507 (2 pages), Biosis database entry only.
Communication pursuant to Rule 164(2)(b) and Article 94(3) EPC issued in European Application No. 18719169.7, dated Jul. 13, 2021, 23 pages.

* cited by examiner

FIG. 2A

```
ATGCTGGTTTTGGTGACCCTGATTTTCTCCTTTTCTGCGAACATCGCATATGCTGACAGC 60
M  L  V  L  V  T  L  I  F  S  F  S  A  N  I  A  Y  A  D  S   20
GAAAGCGACTGCACTGGAAGCGAACCTGTTGACGCCTTCCAAGCTTTCAGTGAGGGCAAA 120
E  S  D  C  T  G  S  E  P  V  D  A  F  Q  A  F  S  E  G  K   40
GAGGCATATGTCCTGGTGAGGTCCACGGATCCCAAAGCGAGGGACTGCTTGAAAGGAGAA 180
E  A  Y  V  L  V  R  S  T  D  P  K  A  R  D  C  L  K  G  E   60
CCAGCCGGAGAAAAGCAGGACAACACGTTGCCGGTGATGATGACGTTTAAGAATGGCACA 240
P  A  G  E  K  Q  D  N  T  L  P  V  M  M  T  F  K  N  G  T   80
GACTGGGCTTCAACCGATTGGACGTTTACTTTGGACGGCGCAAAGGTAACGGCAACCCTT 300
D  W  A  S  T  D  W  T  F  T  L  D  G  A  K  V  T  A  T  L   100
GGTAACCTAACCCAAAATAGGGAAGTGGTCTACGACTCGCAAAGTCATCACTGCCACGTT 360
G  N  L  T  Q  N  R  E  V  V  Y  D  S  Q  S  H  H  C  H  V   120
GACAAGGTCGAGAAGGAAGTTCCAGATTATGAGATGTGGATGCTCGATGCGGGAGGGCTT 420
D  K  V  E  K  E  V  P  D  Y  E  M  W  M  L  D  A  G  G  L   140
GAAGTGGAAGTCGAGTGCTGCCGTCAAAAGCTTGAAGAGTTGGCGTCTGGCAGGAACCAA 480
E  V  E  V  E  C  C  R  Q  K  L  E  E  L  A  S  G  R  N  Q   160
ATGTATCCCCATCTCAAGGACTGCTAG                                  507
M  Y  P  H  L  K  D  C  *                                    168
```

FIG. 2B

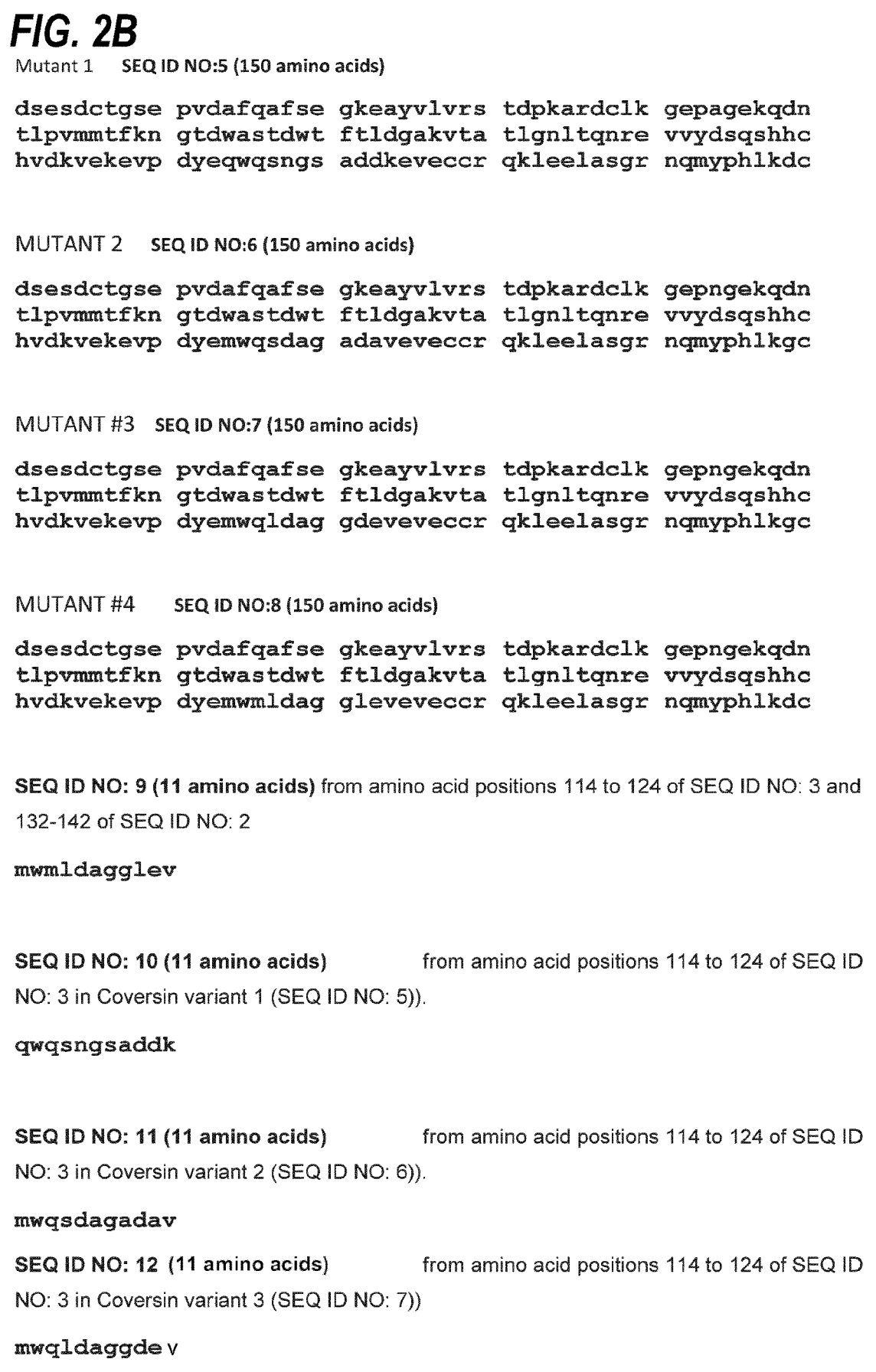

Mutant 1 SEQ ID NO:5 (150 amino acids)

dsesdctgse pvdafqafse gkeayvlvrs tdpkardclk gepagekqdn
tlpvmmtfkn gtdwastdwt ftldgakvta tlgnltqnre vvydsqshhc
hvdkvekevp dyeqwqsngs addkeveccr qkleelasgr nqmyphlkdc

MUTANT 2 SEQ ID NO:6 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwqsdag adaveveccr qkleelasgr nqmyphlkgc

MUTANT #3 SEQ ID NO:7 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwqldag gdeveveccr qkleelasgr nqmyphlkgc

MUTANT #4 SEQ ID NO:8 (150 amino acids)

dsesdctgse pvdafqafse gkeayvlvrs tdpkardclk gepngekqdn
tlpvmmtfkn gtdwastdwt ftldgakvta tlgnltqnre vvydsqshhc
hvdkvekevp dyemwmldag gleveveccr qkleelasgr nqmyphlkdc

SEQ ID NO: 9 (11 amino acids) from amino acid positions 114 to 124 of SEQ ID NO: 3 and 132-142 of SEQ ID NO: 2 mwmldagglev

SEQ ID NO: 10 (11 amino acids) from amino acid positions 114 to 124 of SEQ ID NO: 3 in Coversin variant 1 (SEQ ID NO: 5)).

qwqsngsaddk

SEQ ID NO: 11 (11 amino acids) from amino acid positions 114 to 124 of SEQ ID NO: 3 in Coversin variant 2 (SEQ ID NO: 6)).

mwqsdagadav

SEQ ID NO: 12 (11 amino acids) from amino acid positions 114 to 124 of SEQ ID NO: 3 in Coversin variant 3 (SEQ ID NO: 7))

mwqldaggde v

1: Coversin wt, reduced

2: Coversin variant 1, reduced

3: Coversin variant 2, reduced

FIG. 4B
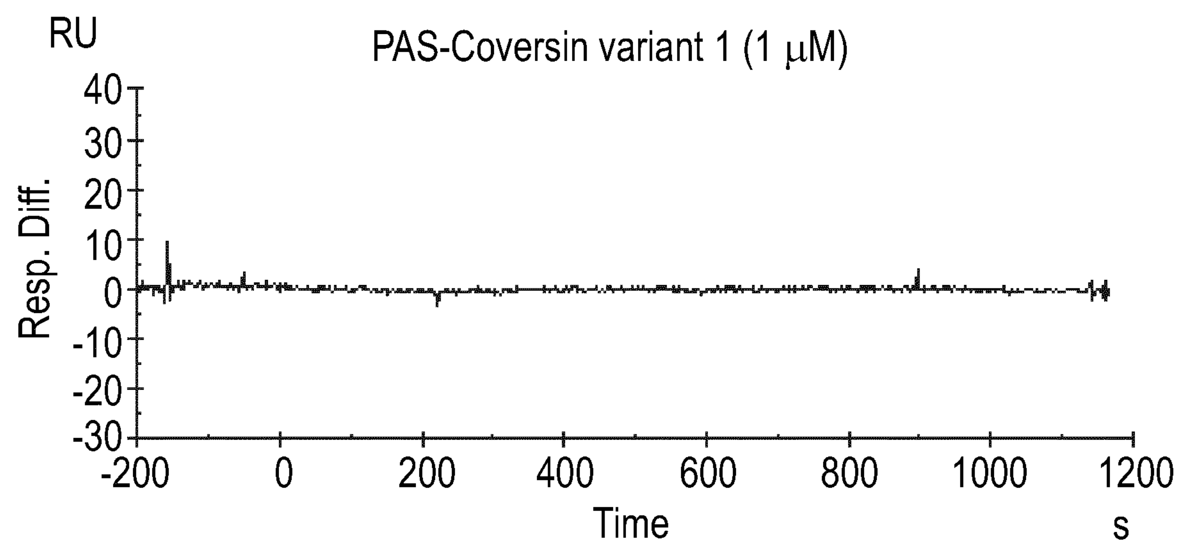
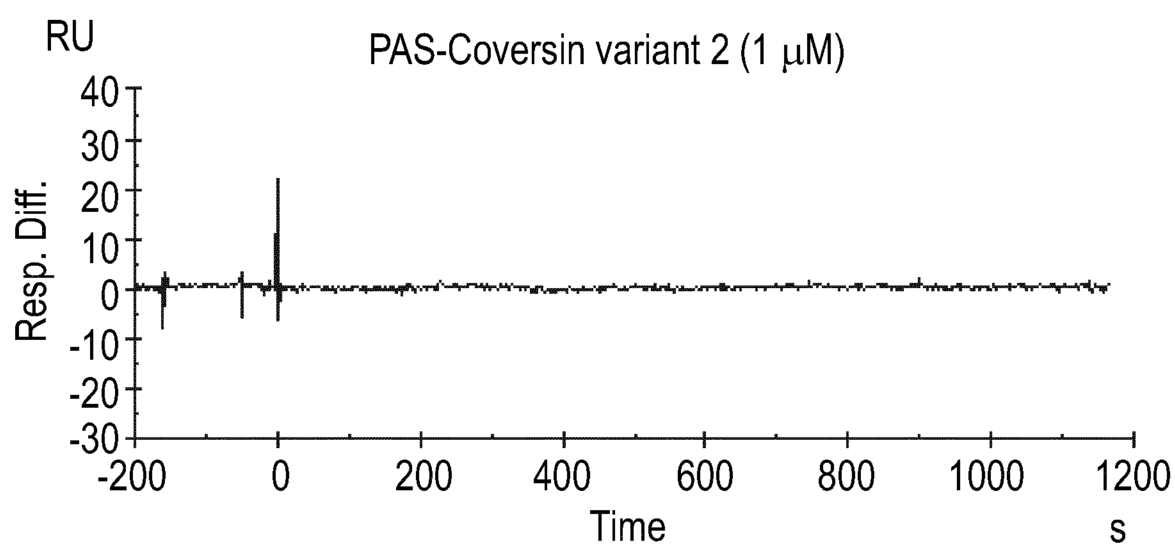

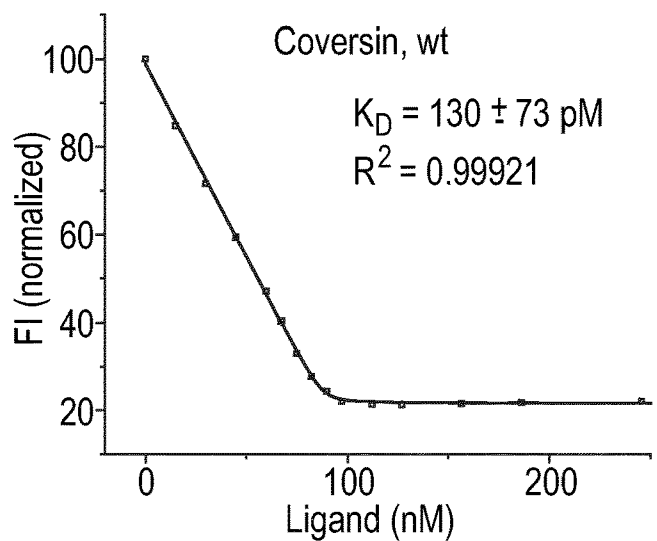
FIG. 5A
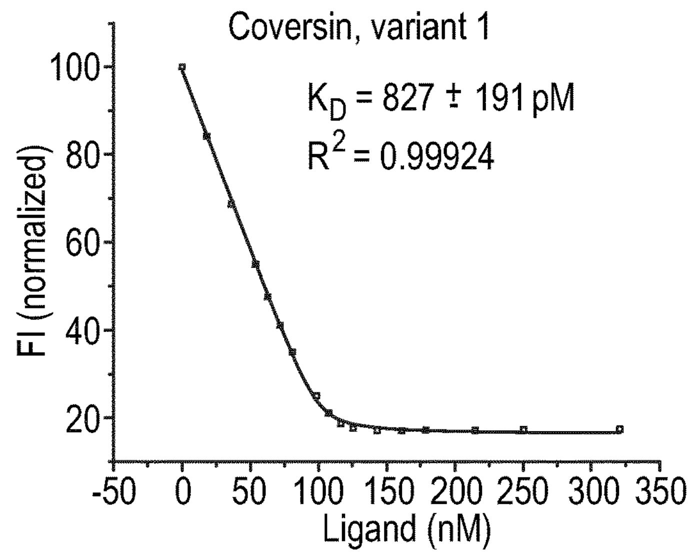
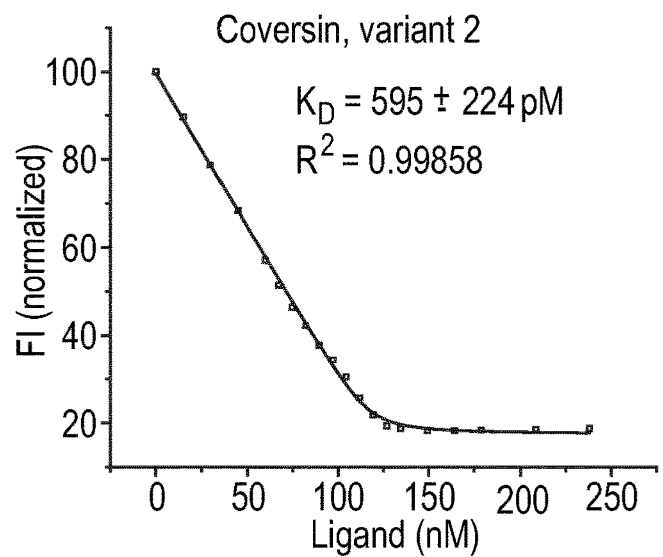

*FIG. 5B*
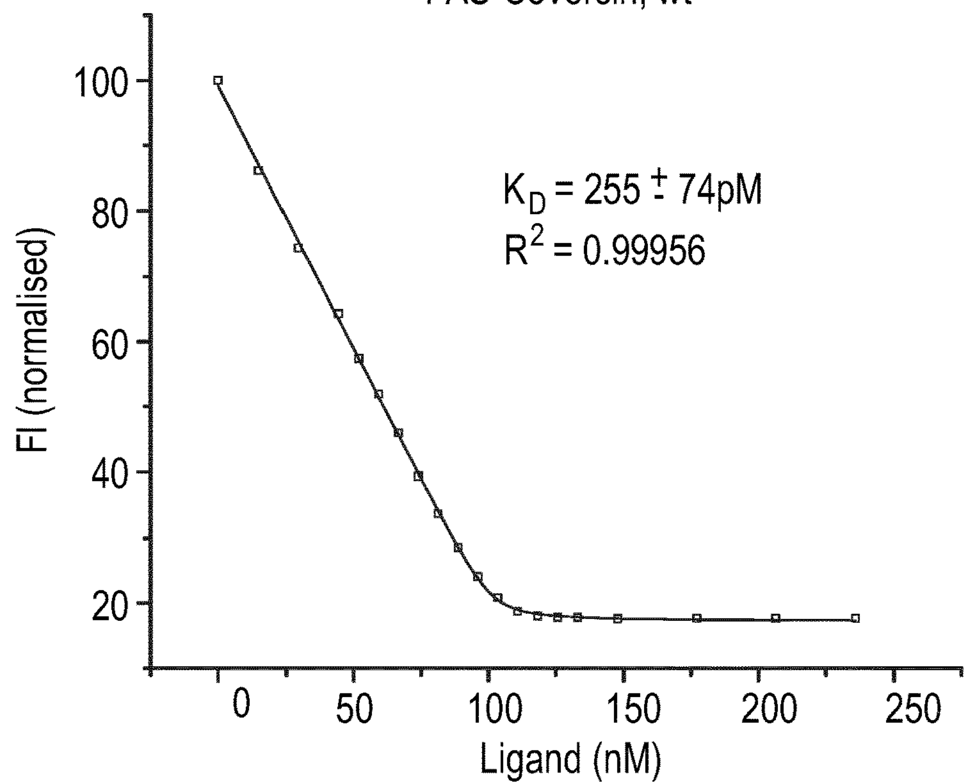
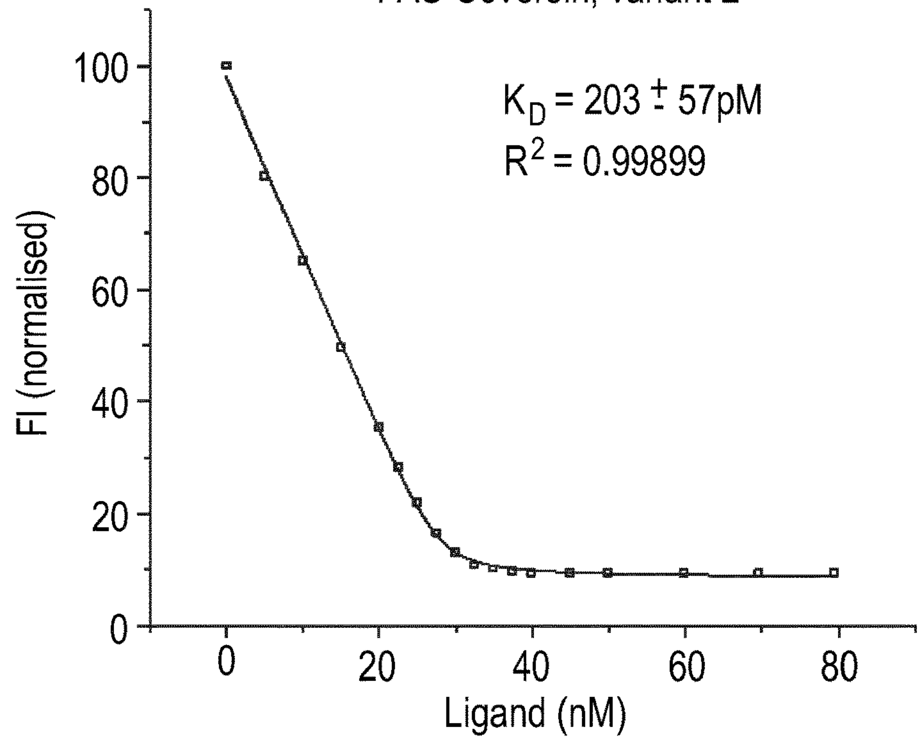

*FIG. 5B (contd)*
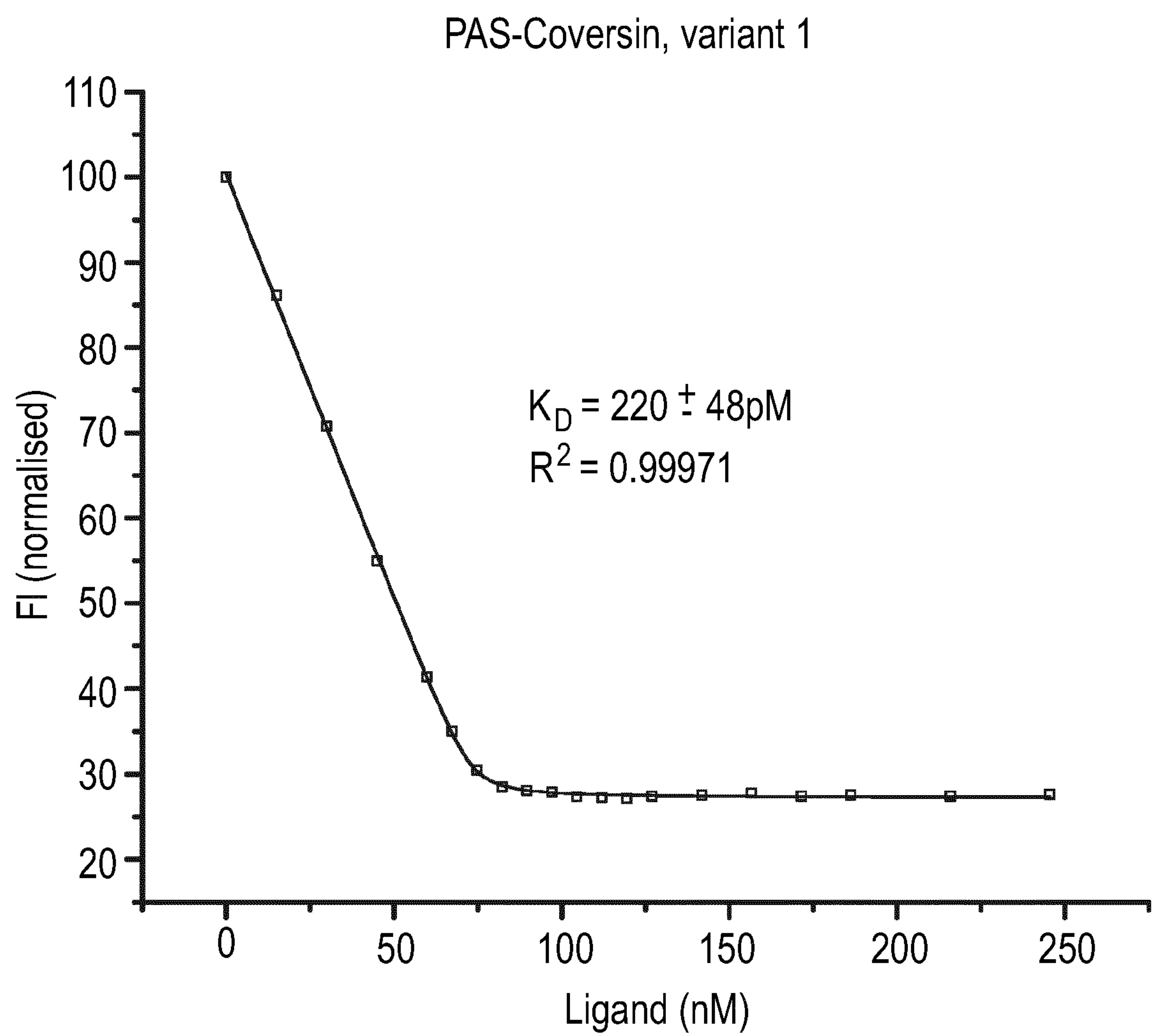

FIG. 6 f(u)
1
0,8
0,6
0,4
0,2
0
Coversin variant #1
Coversin
Coversin variant #2
20 30 40 50 60 70 80 90
Temperature [°C]

| | Melting temperature [°C] |
|---|---|
| Coversin | 61.06 ± 0.03 |
| Coversin variant 2 | 57.83 ± 0.04 |
| Coversin variant 1 | 50.16 ± 0.06 |

FIG. 7

Percentage lysis SRBC in presence of L-Cov1, L-Cov2 and Coversin

Percentage lysis
120
100
80
60
40
20
0
0 1 2 3 4 5 6 7 8 9 10 11 12 13 14
Micrograms protein
Coversin L-Cov1 L-Cov2

COVERSIN VARIANTS LACKING C5 BINDING

CROSS REFERENCE TO RELATED APPLICATIONS

This application is a national phase entry pursuant to 35 U.S.C. § 371 of International Application No. PCT/EP2018/060240, filed Apr. 20, 2018, which claims the benefit of priority of Great Britain Application No. 1706406.4, filed Apr. 21, 2017, each of which is incorporated by reference herein in its entirety for any purpose.

FIELD OF THE INVENTION

The present invention relates to compositions useful in the treatment of diseases and conditions mediated by eicosanoids and in particular to modified tick-derived compounds having leukotriene/hydroxyeicosanoid (LK/E) binding activity for the treatment of diseases and conditions mediated by leukotrienes and hydroxyeicosanoids, and in particular $LTB_4$.

BACKGROUND OF THE INVENTION

Eicosanoids are a family of oxygenated biologically active lipid mediators that are derived from the 20-carbon fatty acid arachidonic acid (AA) through three major enzymatic pathways: cyclooxygenase (COX), lipoxygenase (LO), and cytochrome P450 monooxygenase (CYP450). Eicosanoids include prostanoids (including prostaglandins, PGs, and thromboxanes, TXBs) derived from COX pathway, leukotrienes (LKs) from LO pathway and hydroxyeicosatetraenoic acids (HETEs) and epoxyeicosatrienoic acids (EETs) from LO and P450 monooxygenase pathways (Curtis-Prior, 2004; Peters-Golden & Henderson Jr., 2007). Eicosanoids mediate numerous effects on diverse cell types and organs. These effects include regulation of vascular tone and permeability of capillaries and venules (PGs, TBXs, LKs), contraction or relaxation of muscle (PGs, TBXs, cysteinyl LKs), stimulation or inhibition of platelet function (TBXs, PGs, LKs), regulation of renal blood flow and mineral metabolism (Imig, 2000; Hao and Breyer, 2007), control of growth and or spread of malignant cells (Schwartz et al, 2005; Aya, 2006), and activation of leukocytes in particular in autoimmune and inflammatory conditions (LKs, HETEs) (Samuelsson, 1983; Kim & Luster, 2007).

Leukotriene B4 ($LTB_4$) is the most powerful chemotactic and chemokinetic eicosanoid described and promotes adhesion of neutrophils to the vascular endothelium via upregulation of integrins (Hoover et al, 1984). It is also a complete secretagogue for neutrophils, induces their aggregation and increases microvascular permeability. $LTB_4$ recruits and activates natural killer cells, monocytes and eosinophils. It increases superoxide radical formation (Harrison and Murphy, 1995) and modulates gene expression including production of a number of proinflammatory cytokines and mediators which may augment and prolong tissue inflammation (Ford-Hutchinson, 1990; Showell et al., 1995). $LTB_4$ also has roles in the induction and management of adaptive immune responses. For example regulation of dendritic cell trafficking to draining lymph nodes (Klaas et al, 2005; Del Prete et al, 2007), Th2 cytokine IL-13 production from lung T cells (Miyahara et al, 2006), recruitment of antigen-specific effector CD8+ T cells (Taube et al, 2006) and activation and proliferation of human B lymphocytes (Yamaoka et al, 1989).

Leukotriene $B_4$ ($LTB_4$) and the hydroxyeicosanoids mediate their effects though the BLT1 and BLT2 G-protein coupled receptors (Yokomizo et al, 1997, 2000). Human BLT1 is a high affinity receptor ($K_D$ 0.39-1.5 nM; Tager and Luster, 2003) specific for $LTB_4$ with only 20-hydroxy $LTB_4$ and 12-epi $LTB_4$ able to displace $LTB_4$ in competitive binding studies (Yokomizo et al., 2001). Human BLT2 has a 20-fold lower affinity ($K_D$ 23 nM) for $LTB_4$ than BLT1 and is activated by binding a broader range of eicosanoids including 12-epi $LTB_4$, 20-hydroxy $LTB_4$, 12(S)- and 15(S)-HETE and 12(S)- and 15(S)-HPETE (Yokomizo et al., 2001). Human BLT2 has 45.2 and 44.6% amino acid identity with human and mouse BLT1, while human and mouse BLT2 have 92.7% identity (Yokomizo et al, 2000).

Human BLT1 is mainly expressed on the surface of leukocytes, though it has recently been described in endothelial cells and vascular smooth muscle cells. Human BLT2 is expressed in a broader range of tissue and cell types. A number of specific antagonists of BLT1 and BLT2 have been described which inhibit activation, extravasation and apoptosis of human neutrophils (Kim and Luster, 2007) and reduce symptoms caused by neutrophil infiltration in mouse models of inflammatory arthritis (Kim et al., 2006) and renal ischaemia reperfusion (Noiri et al., 2000). Increasing numbers of studies indicate that both BLT1 and BLT2 can mediate pathological effects through $LTB_4$ and hydroxyeicosanoids (Lundeen et al., 2006), although BLT1 certainly has a dominant role in some pathologies such as collagen induced arthritis in mice (Shao et al, 2006). BLT1−/− deficient mice have also highlighted the importance of BLT1 in directing neutrophil migration in inflammatory responses. In particular, a 5LO deficient mouse strain was used to show autocrine activation of BLT1 on neutrophils is needed for their recruitment into arthritic joints (Chen et al., 2006).

Oxidised isomeric derivatives of $LTB_4$ such as B4 isoleukotrienes are also biologically active (Harrison et al, 1995). As are the hydroxyeicosanoids, for example 5(S)-HETE is a highly potent chemoattractant for eosinophils (Powell and Rokach, 2005). The cysteinyl LKs, which are derived from $LTA_4$, are correlated with the pathophysiology of asthma, including: bronchoconstriction caused by contraction of smooth muscle lining the airways; mucosal edema caused by vascular leakage; increased secretion of mucus; and the presence of an inflammatory-cell infiltrate that is rich in eosinophils (Bisgaard et al., 1985; Drazen et al., 1988).

A number of marketed drugs target the eicosanoids. These include the glucocorticoids which modulate phospholipase A2 ($PLA_2$) and thereby inhibit release of the eicosanoid precursor AA (Sebaldt et al., 1990). Non-steroidal antiinflammatory drugs (NSAID) and other COX2 inhibitors which prevent synthesis of the PGs and TXBs (Curry et al., 2005). There are also a number of LK modifiers which either inhibit the 5-LO enzyme required for $LTB_4$ synthesis (Zileuton; Dube et al., 1998), or antagonise the $CysLT_1$ receptor that mediates the effects of cysteinyl leukotrienes (Zafirlukast and Montelukast) (Sharma and Mohammed, 2006). The LK modifiers are orally available and have been approved by the FDA for use in the treatment of e.g. asthma. No drug that acts specifically on $LTB_4$ or its receptors has yet reached the market.

WO2004/106369 describes a soft tick derived complement (C) inhibitor Coversin that inhibits both the classical, lectin and alternative complement pathways by direct binding to complement component C5 (Nunn et al, 2005). Coversin is derived from the salivary glands of haematophagous arthropods. It has proven therapeutic potential (Hepburn et al, 2007). Coversin prevents complement (C)-mediated activation of C component 5 (C5) in a wide range of mammalian species including humans (Barratt-Due, A., et al. (2011) J. Immunol. 187, 4913-4919)). By binding directly to the CUB, C5d and C5-C345C C5 domains Coversin prevents cleavage of C5 by the C5 complement convertases, thereby preventing release of anaphylatoxin C5a and formation of C5b which nucleates formation of the membrane attack complex (MAC) comprising complement components C5b-9 complex (see e.g. Jore et al. 2016). It has also been shown that Coversin binds to eicosanoids, in particular LKs, especially $LTB_4$ (Roversi, P., et al., (2013) J. Biol. Chem. 2013, 288:18789-18802) enclosing then within the body of the protein. It is known that Coversin can bind $LTB_4$ and C5 simultaneously, and the binding sites are located on opposite faces of Coversin, and the $LTB_4$ binding pocket is fully accessible in the C5-Coversin complex (Jore et al. 2016).

SUMMARY OF THE INVENTION

It has been found that the Coversin polypeptide can be modified to reduce or remove its C5 binding activity (and hence its complement inhibitor activity) while retaining leukotriene/hydroxyeicosanoid (LK/E) binding activity (e.g. LTB4 binding activity). In particular, the present inventors have shown that modifying Coversin polypeptides comprising SEQ ID NO: 3 at specific residues can reduce or remove C5 binding.

The present invention therefore relates to modified versions of Coversin polypeptides comprising SEQ ID NO: 3 which show reduced or no C5 binding but which bind to LK/E, and to polynucleotides encoding such modified Coversin polypeptides.

Such modified Coversin polypeptides, or polynucleotides encoding such modified Coversin polypeptides act as LK/E inhibitors and can be used in the prevention and treatment of diseases and conditions mediated by LK/E. It can be seen that these modified molecules will show reduced or no binding to C5 and as a consequence there will be reduced or no inhibition of the C5 convertase, and reduced or no interference with complement activity.

The invention also relates to the use of the modified Coversin polypeptides and encoding nucleotides of the invention in the treatment and prevention of diseases where leukotrienes, especially $LTB_4$ and hydroxyeicosanoids are implicated in the pathology of the diseases. The modified Coversin polypeptides of the invention can bind to and cage LKs and hydroxyeicosanoids. This may prevent the ligands interacting with both the BLT1 and BLT2 receptors and ameliorate the proinflammatory effects of the fatty acids which have frequently been shown to depend on signaling through both receptors. Thus in accordance with one aspect of the present invention, there is provided the modified Coversin polypeptides and encoding nucleotides of the invention for the treatment of a disease or condition mediated by a leukotriene or hydroxyeicosanoid.

The polypeptides or polynucleotides of the present invention may be used in the treatment of diseases and conditions mediated by a leukotriene or hydroxyeicosanoid. Examples of diseases and disorders which can be treated in accordance with the present invention include contact hypersensitivity, ulcerative colitis, oesophygeal adenocarcinoma, pancreatic adenocarcinoma, breast cancer, acne, aneurysm, periodontal disease, cystic fibrosis, asthma, and bronchiolitis.

Further examples include lung and airways conditions preferably selected from Alpha-1 antitrypsin disease (AATD), pulmonary arterial hypertension (PAH), chronic obstructive pulmonary disease (COPD), bronchiolitis obliterans syndrome (BOS), idiopathic pulmonary disease (IPD), severe persistent asthma, exercise and aspirin induced asthma, allergic rhinitis, and silicosis; skin conditions preferably selected from autoimmune blistering diseases, atopic dermatitis, contact dermatitis, psoriasis, and Churg-Strauss Syndrome; cancers preferably selected from pancreatic cancer, ovarian cancer, colon cancer, prostate cancer, lung cancer, oesophageal cancer, and cancer metastases; eye conditions such as autoimmune uveitis, allergic conjunctivitis, and others listed later in this application. Other general systemic conditions of interest include rheumatoid arthritis, osteoclastic arthritis, post-menopausal osteoporosis, systemic lupus eyrthematosus (SLE), inflammatory bowel disease, vasculitides including Goodpasture's Syndrome and glomerulonephritis, systemic sclerosis, type 2 diabetes, diabetic nephropathy, sickle cell disease (SCD), malaria, trauma, myocardial infarction, obstructive sleep apnea syndrome, atherosclerosis, restenosis after coronary angioplasty, multiple sclerosis (MS), dementia, graft versus host disease (GVHD), and neuropathy.

Most preferably the invention is used in the treatment of AATD, COPD, PAH, asthma e.g. severe persistent asthma, GVHD, blistering skin diseases and psoriasis.

In another aspect of the present invention, there is provided a method of treating or preventing a disease or condition mediated by a leukotriene or hydroxyeicosanoid in a subject in need thereof, the method comprising administering to a subject a therapeutically effective amount of a modified Coversin polypeptide or a polynucleotide encoding a modified Coversin polypeptide according to the present invention.

In a further aspect of the present invention, there is provided a composition comprising a modified Coversin polypeptide and a fatty acid. The fatty acid is preferably a therapeutic fatty acid and is provided for delivery to an individual.

In a further aspect of the present invention there is provided a fusion protein comprising a PAS sequence and the modified Coversin polypeptide of the invention.

DESCRIPTION OF THE FIGURES

FIG. 2 shows (A) Primary sequence of Coversin. Signal sequence underlined. Cysteine residues in bold type. Nucleotide and amino acid number indicated at right. (B) Examples of Coversin variants FIG. 3 shows a reducing SDS-PAGE gel of Coversin wild type (lane 1), Coversin variant 1 (lane 2) and Coversin variant 2 (lane 3) expressed and purified from *E. coli.*

FIG. 5 shows fluorescence titration curves for wild type Coversin and Coversin variants 1 and 2, at various concentrations, binding to $LTB_4$ (A) as well as PASylated versions thereof (B).

FIG. 6 shows thermal denaturation curves for wild type Coversin and Coversin variants 1 and 2 as measured by circular dichroism spectroscopy. A table of values for the melting temperature of each protein is also shown.

FIG. 7 shows the effect of wild type Coversin and Coversin variants 1 and 2 on C5-mediated sheep red blood cell lysis as measured by a CH50 assay. The results of this assay as shown in FIG. 7 are used as an indirect measurement of the capacity of wild type Coversin and variants 1 and 2 to inhibit C5.

DESCRIPTION OF THE SEQUENCES

Figure 1A:
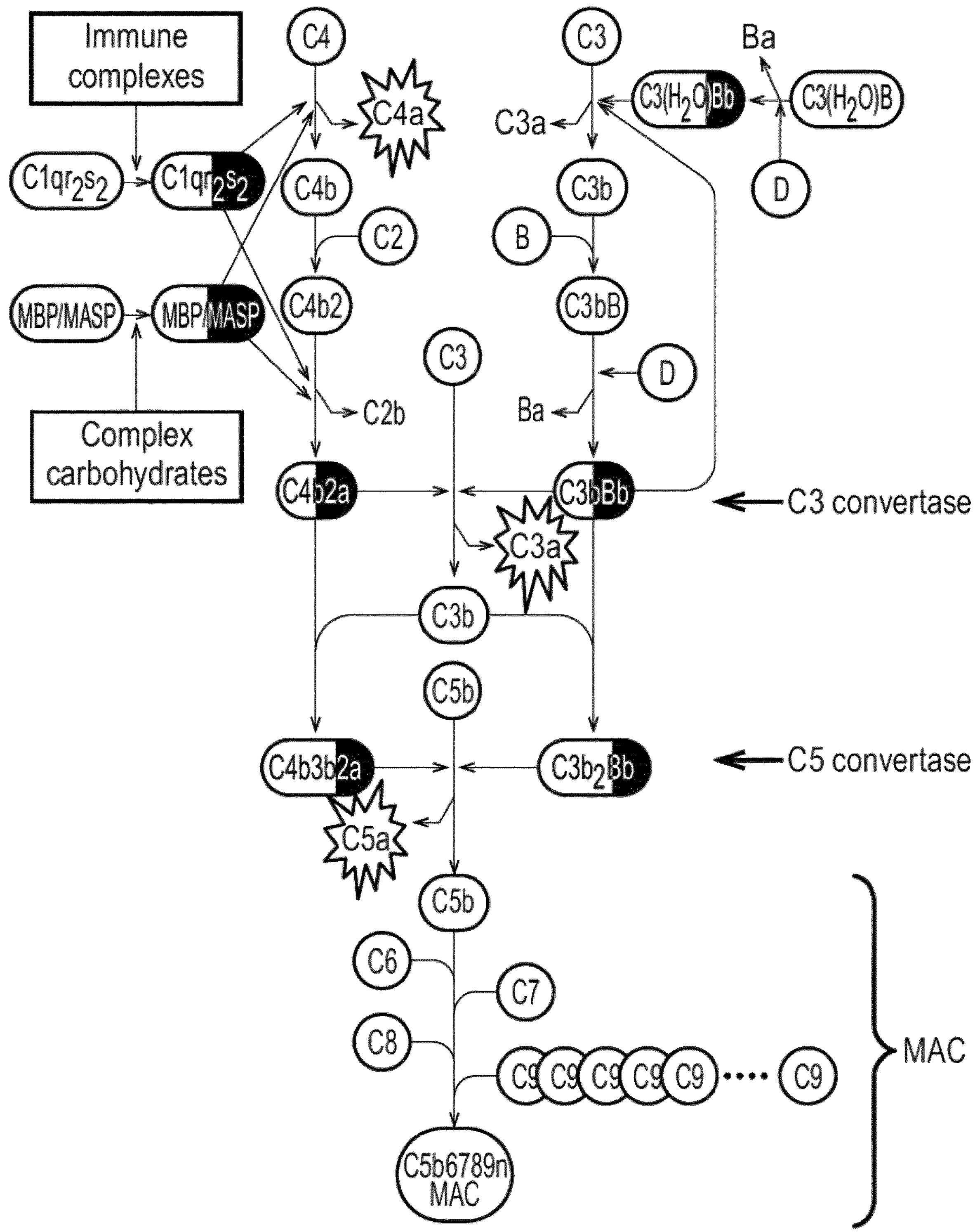
FIG. 1(*a*) shows Schematic diagram of classical and alternative pathways of complement activation. Enzymatic components, dark grey. Anaphylatoxins enclosed in starbursts. (*b*) shows schematic diagram of the eicosanoid pathway.
Figure 1B:
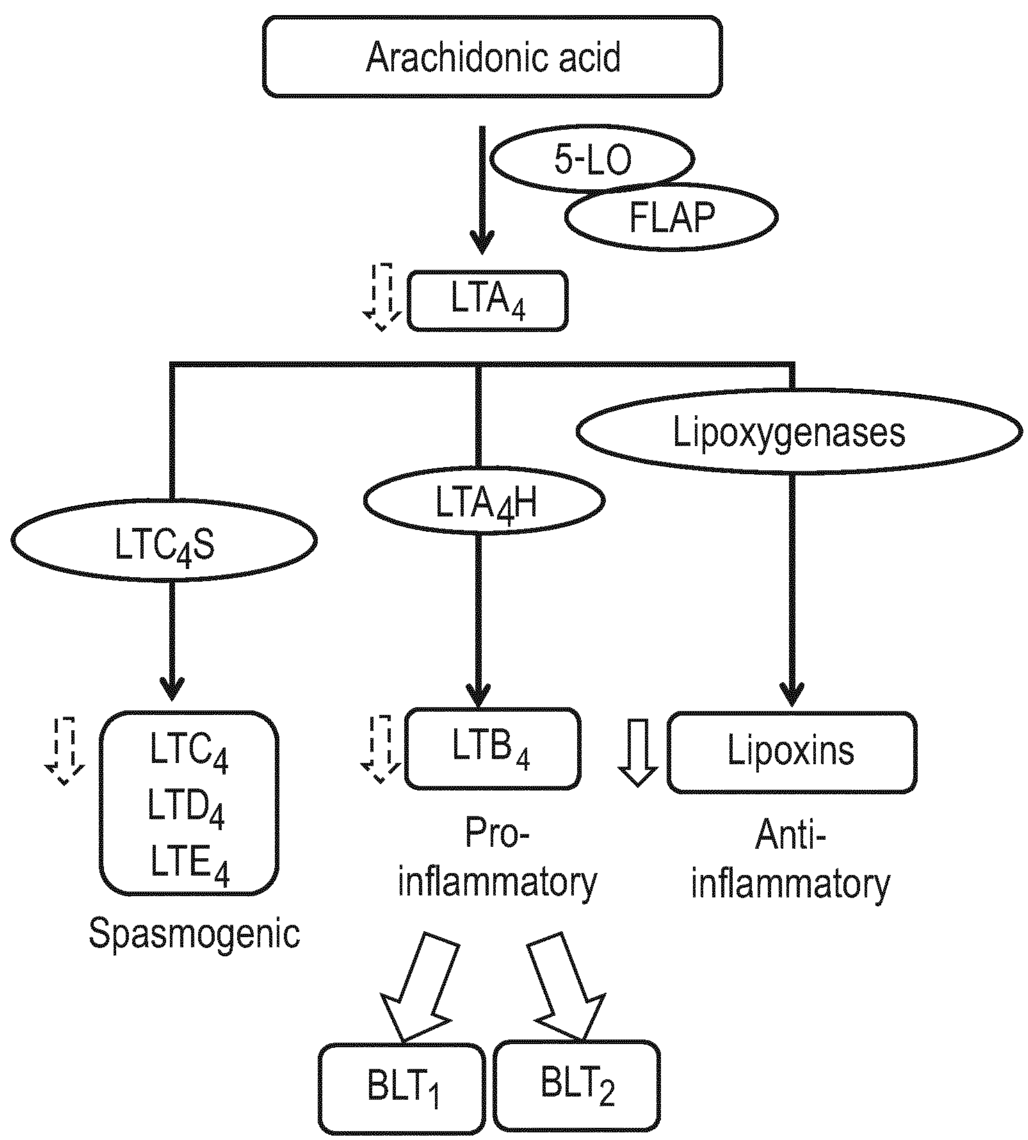

SEQ ID NO: 1 is the polynucleotide sequence of Coversin *Ornithodoros moubata.*

SEQ ID NO: 2 is the amino acid sequence of Coversin *Ornithodoros moubata* (i.e. Amino acids 1-168). The sequence features a loop between beta H and alpha2 at amino acids 132 to 142.

SEQ ID NO: 3 is the amino acid sequence of amino acids 19 to 168 shown in SEQ ID NO: 2 and is the amino acid sequence of Coversin *Ornithodoros moubata* without the first 18 amino acid sequence of the protein of SEQ ID NO: 2, which is a signal sequence. The sequence features a loop between beta H and alpha2 at amino acids 114 to 124.

SEQ ID NO: 4 is the polynucleotide sequence of SEQ ID NO: 3

SEQ ID NO: 5 is the amino acid sequence of a modified Coversin according to the present invention in which SEQ ID NO: 3 has been modified to change Met114 to Gln, Met116 to Gln, Leu117 to Ser, Asp118 to Asn, Ala119 to Gly, Gly120 to Ser, Gly121 to Ala, Leu122 to Asp, Glu123 to Asp and Val124 to Lys. (Coversin variant 1)

SEQ ID NO: 6 is the amino acid sequence of a modified Coversin according to the present invention in which SEQ ID NO: 3 has been modified to change Ala44 to Asn, Met116 to Gln, Leu117 to Ser, Gly121 to Ala, Leu122 to Asp, Glu123 to Ala and Asp149 to Gly. (Coversin variant 2)

SEQ ID NO: 7 is the amino acid sequence of a modified Coversin according to the present invention, modified to change Ala44 to Asn, Met116 to Gln, Leu122 to Asp and Asp149 to Gly. (Coversin variant 3)

SEQ ID NO: 8 is the amino acid sequence of a modified Coversin according to the present invention, modified to change Ala44 to Asn. (Coversin variant 4)

SEQ ID NO: 9 is the amino acid sequence of the loop between beta H and alpha2 at amino acid positions 114 to 124 of SEQ ID NO: 3 (amino acid positions 132-142 of SEQ ID NO: 2).

SEQ ID NO: 10 is the amino acid sequence of the loop between beta H and alpha2 at amino acid positions 114 to 124 of SEQ ID NO: 3 in Coversin variant 1 (SEQ ID NO: 5).

SEQ ID NO: 11 is the amino acid sequence of the loop between beta H and alpha2 at amino acid positions 114 to 124 of SEQ ID NO: 3 in Coversin variant 2 (SEQ ID NO: 6).

SEQ ID NO: 12 is the amino acid sequence of the loop between beta H and alpha2 at amino acid positions 114 to 124 of SEQ ID NO: 3 in Coversin variant 3 (SEQ ID NO: 7).

SEQ ID NOs:13 to 19 are PAS sequences.

DETAILED DESCRIPTION OF THE INVENTION

In one aspect the invention provides a modified Coversin polypeptide which exhibits leukotriene or hydroxyeicosanoid binding activity and reduced or absent C5 binding, said modified Coversin polypeptide comprising SEQ ID NO: 3 in which from 1 to 30 amino acid substitutions are made, wherein (i) in the positions 114 to 124 of SEQ ID NO: 3 one or more of the following substitutions (a)-(j) is made:
  a. Met114 is replaced with Gln, Asp, Asn, Glu, Arg, Lys, Gly, Ala, Pro, His, or Thr;
  b. Met116 is replaced with Gln, Asp, Asn, Glu, Arg, Lys, Gly, Ala, Pro, His, or Thr;
  c. Leu117 is replaced with Ser, Asp, Asn, Glu, Arg, Lys, Gly, Ala, or Pro;
  d. Asp118 is replaced with Asn, Gln, Arg, Lys, Gly, Ala, Leu, Ser, Ile, Phe, Tyr, Met Pro, His, or Thr;
  e. Ala119 is replaced with Gly, Asp, Asn, Glu, Arg, Lys, Leu, Ile, Phe, Tyr, Met, Pro, or His;
  f. Gly120 is replaced with Ser, Asp, Asn, Glu, Arg, Lys, Leu, Ile, Phe, Tyr, Met, Pro, or His;
  g. Gly121 is replaced with Ala, Asp, Asn, Glu, Arg, Lys, Leu, Ile, Phe, Tyr, Met, Pro, or His;
  h. Leu122 is replaced with Asp, Glu, Asn, Ala, Gln, Arg, Lys, Pro, or His;
  i. Glu123 is replaced with Asp, Ala, Gln, Asn, Arg, Lys, Gly, Leu, Ser, Ile, Phe, Tyr, Pro, His, or Thr;
  j. Val124 is replaced with Lys, Gln, Asn, Arg, Lys, Gly, Ala, Pro, His, or Thr; or/and wherein (ii) Ala44 in SEQ ID NO: 3 is replaced with Asn, Asp, Gln, Glu, Arg, Lys, Leu, Ile, Phe, Tyr, Met, Pro, or His;

or a fragment thereof in which up to five amino acids are deleted from the N terminus of the modified Coversin polypeptide.

Also provided is a fusion protein comprising a modified Coversin polypeptide or fragment thereof according to the invention.

Also provided is a nucleic acid molecule encoding a modified Coversin polypeptide or a fragment thereof according to the invention, as well as a vector comprising the nucleic acid molecule according to the invention, and a host cell comprising a nucleic acid molecule according to the invention or a vector according to the invention.

A method for preparing a modified Coversin polypeptide or a fragment thereof according to the invention or a fusion protein according to the invention comprising culturing a host cell according to the invention under conditions whereby said protein is expressed and recovering said protein thus produced is also provided.

A composition comprising a modified Coversin polypeptide according to the invention, a fusion protein according to the invention, or a nucleic acid molecule according to the invention in conjunction with a pharmaceutically acceptable carrier is also provided.

A modified Coversin polypeptide according to the invention, a fusion protein according to the invention, a nucleic acid molecule according to the invention or composition according to the invention for use in therapy is further provided.

A modified Coversin polypeptide according to the invention, a fusion protein according to the invention, a nucleic acid molecule according to the invention or composition according to the invention for use in the treatment of a disease or condition mediated by a leukotriene or hydroxyeicosanoid is also provided, as is a method of treating or preventing a disease or condition mediated by a leukotriene or hydroxyeicosanoid in a subject comprising administering to said subject according to the invention, a fusion protein according to the invention, a nucleic acid molecule according to the invention or composition according to the invention.

In one aspect, the present invention provides modified Coversin polypeptides or polynucleotides encoding said modified Coversin polypeptides for the treatment of a disease or condition mediated by leukotrienes or hydroxyeicosanoids.

Modified Coversin Polypeptides

The modified Coversin polypeptide of the invention is based on a tick-derived complement inhibitor, isolated from the saliva of *Ornithodoros moubata*. This protein was first isolated from the salivary glands of the tick and has been found to inhibit the classical and alternative complement pathways as well as leukotriene and hydroxyeicosanoids, (in particular $LTB_4$). The amino acid sequence for this protein is shown in SEQ ID NO: 2. In some embodiments, a modified Coversin polypeptide according to the invention may be a modified version of the complete sequence shown in SEQ ID NO: 2.

In alternative embodiments, the Coversin polypeptide is provided in a form which does not include the first 18 amino acids of the protein sequence (a signal sequence). Accordingly, a modified Coversin polypeptide according to the invention can be a modified version of SEQ ID NO: 3, that is amino acids 19 to 168 of the amino acid sequence of SEQ ID NO: 2.

Throughout this application, references to a "modified Coversin polypeptide" is to be understood as a reference to a modified version of either SEQ ID NO: 2 or SEQ ID NO: 3 i.e. the Coversin polypeptide with or without the 18 amino acid signal sequence seen at the N-terminus of SEQ ID NO: 2.

Where a particular amino acid within SEQ ID NO: 3 is defined by reference to the number of its position in SEQ ID NO: 3, this amino acid can also be defined by reference to the number of its position in SEQ ID NO: 2 and this number will be 18 greater than for SEQ ID NO: 3 due to the presence of the 18 amino acid signal sequence at the N-terminus of SEQ ID NO: 2.

The amino acid sequence of the modified Coversin polypeptides of the invention varies from that in SEQ ID NO: 2 or SEQ ID NO: 3 by from 1 to 30 amino acids, but retains to some degree the LK/E binding activity as seen with the unmodified Coversin polypeptide. The modified Coversin polypeptides of the invention also exhibit reduced or absent C5 binding compared to the unmodified Coversin polypeptides in SEQ ID NO: 2 and SEQ ID NO: 3. LK/E binding activity as used herein refers to the ability to bind to leukotrienes and hydroxyeicosanoids including but not limited to $LTB_4$, B4 isoleukotrienes and any hydroxylated derivative thereof, HETEs, HPETEs and EETs. $LTB_4$ binding is of particular interest.

The modified Coversin polypeptides of the invention may consist of SEQ ID NO: 2 or 3, modified in accordance with the description below, or may comprise SEQ ID NO: 2 or 3, modified in accordance with the description below.

The unmodified Coversin polypeptide in SEQ ID NO: 2 and SEQ ID NO: 3 features a loop between beta H and alpha2 at amino acid positions 114 to 124 of SEQ ID NO: 3 (amino acid positions 132-142 of SEQ ID NO: 2). This loop has the sequence shown below:

```
                                    (SEQ ID NO: 9)
-Met-Trp-Met-Leu-Asp-Ala-Gly-Gly-Leu-Glu-Val-
```

The first Met is at position 114 of SEQ ID NO: 3 and at position 132 of SEQ ID NO: 2.

In one aspect of the invention the Coversin polypeptide in SEQ ID NO: 2 or SEQ ID NO: 3 is modified such that at positions 114 to 124 of SEQ ID NO: 3 one or more of the following substitutions (a)-(j) is made:

a. Met114 is replaced with Gln, Asp, Asn, Glu, Arg, Lys, Gly, Ala, Pro, His, or Thr, preferably Gln or Ala;
b. Met116 is replaced with Gln, Asp, Asn, Glu, Arg, Lys, Gly, Ala, Pro, His, or Thr, preferably Gln or Ala;
c. Leu117 is replaced with Ser, Asp, Asn, Glu, Arg, Lys, Gly, Ala, or Pro, preferably Ser or Ala;
d. Asp118 is replaced with Asn, Gln, Arg, Lys, Gly, Ala, Leu, Ser, Ile, Phe, Tyr, Met Pro, His, or Thr, preferably Asn;
e. Ala119 is replaced with Gly, Asp, Asn, Glu, Arg, Lys, Leu, Ile, Phe, Tyr, Met, Pro, or His, preferably Gly or Asn;
f. Gly120 is replaced with Ser, Asp, Asn, Glu, Arg, Lys, Leu, Ile, Phe, Tyr, Met, Pro, or His, preferably Ser or Asn;
g. Gly121 is replaced with Ala, Asp, Asn, Glu, Arg, Lys, Leu, Ile, Phe, Tyr, Met, Pro, or His, preferably Ala or Asn;
h. Leu122 is replaced with Asp, Glu, Asn, Ala, Gln, Arg, Lys, Pro, or His, preferably Asp or Ala;
i. Glu123 is replaced with Asp, Ala, Gln, Asn, Arg, Lys, Gly, Leu, Ser, Ile, Phe, Tyr, Pro, His, or Thr, preferably Asp, Ala, Gln or Asn;
j. Val124 is replaced with Lys, Gln, Asn, Arg, Lys, Gly, Ala, Pro, His, or Thr, preferably Lys or Ala.

In embodiments of the present invention, the Coversin polypeptide in SEQ ID NO: 2 or SEQ ID NO: 3 is modified such that at positions 114 to 124 of SEQ ID NO: 3 one or more of the following substitutions (a)-(j) is made:

a. Met114 is replaced with Gln;
b. Met116 is replaced with Gln;
c. Leu117 is replaced with Ser;
d. Asp118 is replaced with Asn;
e. Ala119 is replaced with Gly;
f. Gly120 is replaced with Ser;
g. Gly121 is replaced with Ala;
h. Leu122 is replaced with Asp;
i. Glu123 is replaced with Asp, or Ala;
j. Val124 is replaced with Lys.

In embodiments of the present invention, the Coversin polypeptide in SEQ ID NO: 2 or SEQ ID NO: 3 is modified such that at positions 114 to 124 of SEQ ID NO: 3 one or more of the following substitutions (a)-(j) is made:

a. Met114 is replaced with Ala;
b. Met116 is replaced with Ala;
c. Leu117 is replaced with Ala;
d. Asp118 is replaced with Asn;
e. Ala119 is replaced with Asn;
f. Gly120 is replaced with Asn;
g. Gly121 is replaced with Asn;
h. Leu122 is replaced with Ala;

i. Glu123 is replaced with Gln, or Asn;

j. Val124 is replaced with Ala.

In embodiments of the present invention, two, three, four, five, six, seven, eight, nine, or ten of the substitutions (a)-(j) are present. Preferably two or more, five or more, or eight or more of the substitutions (a)-(j) are present.

In some embodiments, the Coversin polypeptide in SEQ ID NO: 2 or SEQ ID NO: 3 is modified such that at positions 114 to 124 of SEQ ID NO: 3 the following substitutions are present:

a. Met114 is replaced with Gln;
b. Met116 is replaced with Gln;
c. Leu117 is replaced with Ser;
d. Asp118 is replaced with Asn;
e. Ala119 is replaced with Gly;
f. Gly120 is replaced with Ser;
g. Gly121 is replaced with Ala;
h. Leu122 is replaced with Asp;
i. Glu123 is replaced with Asp;
j. Val124 is replaced with Lys.

Optionally in the modified Coversin polypeptide referred to above Trp115 is not substituted. A preferred modified Coversin polypeptide has a loop between beta H and alpha2 at amino acid positions 114 to 124 of SEQ ID NO: 3 that has the sequence Gln-Trp-Gln-Ser-Asn-Gly-Ser-Ala-Asp-Asp-Lys (SEQ ID NO:10).

In some embodiments, the Coversin polypeptide is modified such that at positions 114 to 124 of SEQ ID NO: 3 the following substitutions are present:

a. Met114 is replaced with Gln, Asp, Asn, Glu, Arg, Lys, Gly, Ala, Pro, His, or Thr, preferably Gln;
b. Leu117 is replaced with Ser, Asp, Asn, Glu, Arg, Lys, Gly, Ala, or Pro, preferably Ser;
c. Gly121 is replaced with Ala, Asp, Glu, Arg, Lys, Leu, Ile, Phe, Tyr, Met, Pro, or His, preferably Ala;
d. Leu122 is replaced with Asp, Glu, Asn, Gln, Arg, Lys, Pro, or His, preferably Asp;
e. Glu123 is replaced with Asp, Ala, Gln, Asn, Arg, Lys, Gly, Leu, Ser, Ile, Phe, Tyr, Pro, His, or Thr, preferably Asp or Ala, more preferably Ala.

In more particular embodiments;

a. Met116 is replaced with Gln;
b. Leu117 is replaced with Ser;
c. Gly121 is replaced with Ala;
d. Leu122 is replaced with Asp;
e. Glu123 is replaced with Ala.

Optionally in this modified Coversin polypeptide referred to above Trp 115 is not substituted. Optionally in this embodiment Met114, Trp 115, Asp118, Ala119, Gly120 and Val124 are not substituted, or are substituted with conservative substitutions as referred to elsewhere herein. A preferred modified Coversin polypeptide has a loop between beta H and alpha2 at amino acid positions 114 to 124 of SEQ ID NO: 3 that has the sequence Met-Trp-Gln-Ser-Asp-Ala-Gly-Ala-Asp-Ala-Val (SEQ ID NO:11).

In some embodiments, the Coversin polypeptide is modified such that at positions 114 to 124 of SEQ ID NO: 3 the following substitutions are present:

a. Met116 is replaced with Gln, Asp, Asn, Glu, Arg, Lys, Gly, Ala, Pro, His, or Thr, preferably Gln;
b. Leu122 is replaced with Asp, Glu, Asn, Gln, Arg, Lys, Pro, or His, preferably Asp;

In more particular embodiments;

a. Met116 is replaced with Gln;
b. Leu122 is replaced with Asp.

Optionally in this modified Coversin polypeptide referred to above Trp 115 is not substituted. Optionally in this embodiment Met114, Trp 115, Leu117, Asp118, Ala119, Gly120, Gly121, Glu123 and Val124 are not substituted. A preferred modified Coversin polypeptide has a loop between beta H and alpha2 at amino acid positions 114 to 124 of SEQ ID NO: 3 that has the sequence Met-Trp-Gln-Leu-Asp-Ala-Gly-Gly-Asp-Glu-Val (SEQ ID NO:12).

In another aspect of the invention the Coversin polypeptide is modified such that Ala44 in SEQ ID NO: 3 (Ala62 in SEQ ID NO: 2) is replaced with Asn, Asp, Gln, Glu, Arg, Lys, Leu, Ile, Phe, Tyr, Met, Pro, or His.

In preferred embodiments Ala44 in SEQ ID NO: 3 is replaced with Asn.

This substitution at position 44 of SEQ ID NO: 3 (or position 62 of SEQ ID NO: 2) may be made in combination with any of the other substitutions referred to herein.

In another aspect of the invention the Coversin polypeptide is modified such that at positions 114 to 124 of SEQ ID NO: 3 one or more of the following substitutions (a)-(j) is present:

a. Met114 is replaced with Gln, Asp, Asn, Glu, Arg, Lys, Gly, Ala, Pro, His, or Thr, preferably Gln or Ala, e.g. Gln;
b. Met116 is replaced with Gln, Asp, Asn, Glu, Arg, Lys, Gly, Ala, Pro, His, or Thr, preferably Gln or Ala e.g. Gln;
c. Leu117 is replaced with Ser, Asp, Asn, Glu, Arg, Lys, Gly, Ala, or Pro, preferably Ser or Ala, e.g. Ser;
d. Asp118 is replaced with Asn, Gln, Arg, Lys, Gly, Ala, Leu, Ser, Ile, Phe, Tyr, Met Pro, His, or Thr, preferably Asn;
e. Ala119 is replaced with Gly, Asp, Glu, Arg, Lys, Leu, Ile, Phe, Tyr, Met, Pro, or His, preferably Gly or Asn, e.g. Gly;
f. Gly120 is replaced with Ser, Asp, Glu, Arg, Lys, Leu, Ile, Phe, Tyr, Met, Pro, or His, preferably Ser or Asn, e.g. Ser;
g. Gly121 is replaced with Ala, Asp, Glu, Arg, Lys, Leu, Ile, Phe, Tyr, Met, Pro, or His preferably Ala or Asn, e.g. Ala;
h. Leu122 is replaced with Asp, Glu, Asn, Gln, Arg, Lys, Pro, or His, preferably Asp or Ala, e.g. Asp;
i. Glu123 is replaced with Asp, Ala, Gln, Asn, Arg, Lys, Gly, Leu, Ser, Ile, Phe, Tyr, Pro, His, or Thr, preferably Asp, Ala, Gln or Asn, e.g. Asp or Ala;
j. Val124 is replaced with Lys, Gln, Asn, Arg, Lys, Gly, Ala, Pro, His, or Thr, preferably Lys or Ala, e.g. Lys;

and additionally Ala44 in SEQ ID NO: 3 (Ala62 in SEQ ID NO: 2) is replaced with Asn, Asp, Gln, Glu, Arg, Lys, Leu, Ile, Phe, Tyr, Met, Pro, or His, preferably Asn.

In some embodiments, the Coversin polypeptide is modified such that at positions 114 to 124 of SEQ ID NO: 3 the following substitutions are present:

a. Met116 is replaced with Gln;
b. Leu117 is replaced with Ser;
c. Gly121 is replaced with Ala;
d. Leu122 is replaced with Asp;
e. Glu123 is replaced with Ala;

and Ala44 in SEQ ID NO: 3 is replaced with Asn.

In preferred aspects of this embodiment the amino acid residues corresponding to positions 114 to 124 of SEQ ID NO: 3 are as set out in SEQ ID NO: 11.

In some embodiments, the Coversin polypeptide is modified such that at positions 114 to 124 of SEQ ID NO: 3 the following substitutions are present:

a. Met116 is replaced with Gln;
b. Leu122 is replaced with Asp;

and Ala44 in SEQ ID NO: 3 is replaced with Asn

In preferred aspects of this embodiment the amino acid residues corresponding to positions 114 to 124 of SEQ ID NO: 3 are as set out in SEQ ID NO:12.

In some embodiments the Coversin polypeptide is modified such that Asp149 in SEQ ID NO: 3 is replaced with Gly, Gln, Asn, Ala, Met, Arg, Lys, Leu, Ser, Ile, Phe, Tyr, Pro, His, or Thr. In some embodiments the Coversin polypeptide is modified such that Asp149 of SEQ ID NO: 3 is replaced with Gly. This substitution at position 149 of SEQ ID NO: 3 (position 167 of SEQ ID NO: 2) may be made in combination with any of the other substitutions referred to herein.

In some embodiments, the Coversin polypeptide is modified such that at positions 114 to 124 of SEQ ID NO: 3 the following substitutions are present:

a. Met116 is replaced with Gln;
b. Leu117 is replaced with Ser;
c. Gly121 is replaced with Ala;
d. Leu122 is replaced with Asp;
e. Glu123 is replaced with Ala;

Ala44 in SEQ ID NO: 3 is replaced with Asn and Asp149 of SEQ ID NO: 3 is replaced with Gly149.

In preferred aspects of this embodiment the amino acid residues corresponding to positions 114 to 124 of SEQ ID NO: 3 are as set out in SEQ ID NO:11.

In some embodiments, the Coversin polypeptide is modified such that at positions 114 to 124 of SEQ ID NO: 3 the following substitutions are present:

a. Met116 is replaced with Gln;
b. Leu122 is replaced with Asp;

Ala44 in SEQ ID NO: 3 is replaced with Asn and Asp149 of SEQ ID NO: 3 is replaced with Gly149.

In preferred aspects of this embodiment the amino acid residues corresponding to positions 114 to 124 of SEQ ID NO:3 are as set out in SEQ ID NO:12.

In the various aspects and embodiments of this disclosure, the modified Coversin polypeptides of the invention differ from the unmodified Coversin polypeptides in SEQ ID NO: 2 and SEQ ID NO: 3 by from 1 to 30 amino acids. Any modifications may be made to the Coversin polypeptide in SEQ ID NO: 2 and SEQ ID NO: 3 provided that the resulting modified Coversin polypeptide exhibits LK/E binding activity and reduced or absent C5 binding, compared to the unmodified Coversin polypeptide.

In some embodiments, of the invention the six cysteine amino acids at positions 6, 38, 100, 128, 129, 150 of SEQ ID NO: 3 are retained in the modified Coversin polypeptides of the invention.

In some embodiments, Asn60 and Asn84 in SEQ ID NO: 3 are each replaced with Gln. This modification can be carried out by site directed mutagenesis to prevent N-linked hyperglycosylation when the polypeptide is expressed in eukaryotic cells (e.g. yeast, plant, mammalian).

In some embodiments one or more of the following amino acids in SEQ ID NO: 3 are thought to be involved in binding to $LTB_4$ and may therefore be retained in unmodified form: Phe18, Tyr25, Arg36, Leu39, Gly41, Pro43, Leu52, Val54, Met56, Phe58, Thr67, Trp69, Phe71, Gln87, Arg89, His99, His101, Asp103, and Trp115. In some embodiments, at least five, ten or fifteen, or all of these amino acids are retained in unmodified form in the modified Coversin polypeptides of the invention. In some embodiments one or more of these amino acids may be conservatively substituted. In some embodiments up to five, ten or fifteen, or all of these amino acids are conservatively substituted in the modified Coversin polypeptides of the invention.

Amino acids at the following positions in SEQ ID NO: 3 are highly conserved between Coversin and TSGP2 and TSGP3: 5, 6, 11, 13-15, 20-21, 24-27, 29-32, 35-41, 45, 47-48, 50, 52-60, 64, 66, 69-81, 83, 84, 86, 90-94, 97-104, 112-113, 115, 125-129, 132-139, 145, 148, and 150.

Amino acids at the following positions in SEQ ID NO: 3 are thought to be involved in binding to LTB4 and/or are highly conserved between Coversin and TSGP2 and TSGP3: 5, 6, 11, 13-15, 18, 20-21, 24-27, 29-32, 35-41, 43, 45, 47-48, 50, 52-60, 64, 66, 67, 69-81, 83, 84, 86, 87, 89, 90-94, 97-104, 112-113, 115, 125-129, 132-139, 145, 148, and 150.

Amino acids at the following positions in SEQ ID NO: 3 are thought to be involved in binding to LTB4 and/or are highly conserved between Coversin and TSGP2 and TSGP3: 5, 6, 11, 13-15, 18, 20-21, 24-25, 27, 30-32, 35-41, 43, 47-48, 50, 52-60, 64, 66, 67, 69-81, 83, 84, 86, 87, 89, 90-94, 98, 100, 102-104, 112-113, 115, 126, 128-129, 132-139, 145, 148, and 150.

In some embodiments therefore the above amino acids are retained in unmodified form. In some embodiments, at least five, ten or fifteen, or all of these amino acids are retained in unmodified form in the modified Coversin polypeptides of the invention. In some embodiments one or more of these amino acids may be conservatively substituted. In some embodiments up to five, ten or fifteen, twenty, twenty five, 30, 40, 50 or all of these amino acids are conservatively substituted in the modified Coversin polypeptides of the invention The modified Coversin polypeptides of the invention typically differ from SEQ ID NO: 2 or SEQ ID NO: 3 by from 1 to 30, preferably from 2 to 25, more preferably from 3 to 20, even more preferably from 4 to 15 amino acids. Typically the difference will be 5 to 12, or 6 to 10 amino acid changes. For example, from 1 to 30, or 2 to 25, 3 to 30, 4 to 15, 5 to 12, or 6 to 10 amino acid substitutions may be made in SEQ ID NO: 2 or SEQ ID NO: 3.

Modified Coversin polypeptides which have the loop between beta H and alpha2 at amino acid positions 114 to 124 of SEQ ID NO: 3 (amino acid positions 132-142 of SEQ ID NO: 2) as set out in SEQ ID NO: 10 have 10 amino acid substitutions compared to SEQ ID NO: 3 as a result of the presence of this loop. In some embodiments, the modified Coversin polypeptides of the invention preferably therefore have 1-15, 2-10, 3-5, or up to 2, 3, 4 or 5 additional substitutions compared to SEQ ID NO: 3 beyond those that are set out in SEQ ID NO: 5 (e.g. in the loop of SEQ ID NO: 10).

Modified Coversin polypeptides which have the loop between beta H and alpha2 at amino acid positions 114 to 124 of SEQ ID NO: 3 (amino acid positions 132-142 of SEQ ID NO: 2) as set out in SEQ ID NO: 11 have 5 amino acid substitutions compared to SEQ ID NO: 3 as a result of the presence of this loop. In some embodiments, the modified Coversin polypeptides of the invention preferably therefore have 1-20, 2-15, 3-10, or up to 2, 3, 4, 5, 6, 7, 8, 9, 10 additional substitutions compared to SEQ ID NO: 3 beyond those that are set out in SEQ ID NO: 6 (e.g. in the loop of SEQ ID NO: 11). The additional substitutions preferably include substitutions at position 44 and 149, as set out elsewhere herein.

Modified Coversin polypeptides which have the loop between beta H and alpha2 at amino acid positions 114 to 124 of SEQ ID NO: 3 (amino acid positions 132-142 of SEQ ID NO: 2) as set out in SEQ ID NO: 12 have 2 amino acid substitutions compared to SEQ ID NO:3 as a result of the presence of this loop. In some embodiments, the modified Coversin polypeptides of the invention preferably therefore have 1-25, 2-12, 3-15, or up to 2, 3, 4, 5, 6, 7, 8, 9, 10, 11, 12, 13, 14, 15 additional substitutions compared to SEQ ID NO: 3 beyond those that are set out in SEQ ID NO: 7 (e.g. substitutions in the loop of SEQ ID NO: 12). The additional substitutions preferably include substitutions at position 44 and 149, as set out elsewhere herein.

Modified Coversin polypeptides which have the substitution at position 44 of SEQ ID NO:3 as set out elsewhere herein preferably have 1-25, 2-12, 3-15, or up to 2, 3, 4, 5, 6, 7, 8, 9, 10, 11, 12, 13, 14, 15 additional substitutions compared to SEQ ID NO:3.

Substitutions other than those explicitly referred to above are preferably conservative substitutions, for example according to the following Table. Amino acids in the same block in the second column and preferably in the same line in the third column may be substituted for each other:

| | | |
|---|---|---|
| Aliphatic | Non-polar | G A P |
| | | I L V |
| | Polar - uncharged | C S T M |
| | | N Q |
| | Polar - charged | D E |
| | | K R |
| Aromatic | | H F W Y |

Substitutions may also be selected based on residues that are found in variants, such as a homologue of the Coversin protein obtained from *Ornithodoros moubata*. Such homologues may include paralogues and orthologues of the Coversin sequence that is set out in SEQ ID NO: 2 or 3, including, for example, the Coversin protein sequence from other tick species including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus*, and *O. savignyi*.

The present invention also encompasses fragments of the modified Coversin polypeptide of SEQ ID NO: 3 in which up to five amino acids are deleted from the N terminus of the modified Coversin polypeptide. The fragment may correspond to 1, 2, 3, 4 or 5 deletions from the N terminus of the modified Coversin polypeptide. Deletions from other positions in the amino acid sequence of SEQ ID NO: 2 or SEQ ID NO: 3 are also envisaged as forming part of the invention, if the resulting polypeptide retains the LK/E binding activity of the modified Coversin (e.g. as described herein in relation to the modified polypeptides) and has reduced or absent complement inhibitor activity (e.g. as described herein in relation to the modified polypeptides).

The modified Coversin polypeptides of the invention may also be provided as a fusion protein comprising the modified Coversin polypeptide genetically or chemically fused to another peptide. A fusion protein may be obtained, for example, by cloning a polynucleotide encoding the modified Coversin polypeptide in frame to the coding sequences for a heterologous protein sequence. The term "heterologous", when used herein, is intended to designate any polypeptide other than the modified Coversin polypeptide of the invention. Examples of heterologous sequences, that can be comprised in the soluble fusion proteins either at N- or at C-terminus, are the following: extracellular domains of membrane-bound protein, immunoglobulin constant regions (Fc region), PAS or XTEN or other similar unstructured polypeptides, multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them. Examples of such additional properties are a longer lasting half-life in body fluids (e.g. resulting from the addition of an Fc region or Pasylation (Schlapschy M, et al Protein Eng Des Sel. 2013 August; 26(8):489-501), the extracellular localization, or an easier purification procedure as allowed by a tag such as a histidine, GST, FLAG, avidin or HA tag. Fusion proteins may additionally contain linker sequences (e.g. 1-50, 2-30, 3-20, 5-10 amino acids in length), such that the components are separated by this linker.

Fusion proteins are thus examples of proteins comprising modified Coversin polypeptides, and include by way of specific example a protein comprising a PAS sequence and a modified Coversin polypeptide sequence. PAS sequences are described e.g. in Schlapschy M, et al Protein Eng Des Sel. 2013 August; 26(8):489-501, and EP 08773567.6, with a PASylated Coversin molecule being described in Kuhn et al Bioconjugate Chem., 2016, 27 (10), pp 2359-2371. PASylation describes the genetic fusion of a protein with conformationally disordered polypeptide sequences composed of the amino acids Pro, Ala, and/or Ser. This is a technology developed by XL Protein (http://xl-protein.com/) and provides a simple way to attach a solvated random chain with large hydrodynamic volume to the protein to which it is fused. The polypeptide sequence adopts a bulky random coil structure. The size of the resulting fusion protein is thus much bigger than the protein to which it is fused. This has been shown to reduce clearance in biological systems. Appropriate PAS sequences are described in EP08773567.6, as well as the Schlapschy reference above. Any suitable PAS sequence may be used in the fusion protein. Examples include an amino acid sequence consisting of at least about 100 amino acid residues forming a random coil conformation and consisting of alanine, serine and proline residues (or consisting of proline and alanine residues). This may comprise a plurality of amino acid repeats, wherein said repeats consist of Ala, Ser, and Pro residues (or proline and alanine residues) and wherein no more than 6 consecutive amino acid residues are identical. Proline residues may constitute more than 4% and less than 40% of the amino acids of the sequence. The sequence may comprise an amino acid sequence selected from:

```
                                   (SEQ ID NO: 13)
ASPAAPAPASPAAPAPSAPA;

                                   (SEQ ID NO: 14)
AAPASPAPAAPSAPAPAAPS;

                                   (SEQ ID NO: 15)
APSSPSPSAPSSPSPASPSS,

                                   (SEQ ID NO: 16)
SAPSSPSPSAPSSPSPASPS,

                                   (SEQ ID NO: 17)
SSPSAPSPSSPASPSPSSPA,

                                   (SEQ ID NO: 18)
AASPAAPSAPPAAASPAAPSAPPA
and

                                   (SEQ ID NO: 19)
ASAAAPAAASAAASAPSAAA
```

or circular permuted versions or multimers of these sequences as a whole or parts of these sequences. There may, for example be 5-40, 10-30, 15-25, 18-20 preferably 20-30 or 30 copies of one of the repeats present in the PAS sequence, i.e. one of SEQ ID NOs 13-19, preferably 13. Preferably the PAS sequence comprises or consists of 30 copies of SEQ ID NO:13. Preferably the PAS sequence is fused to the N terminus of the Coversin-type protein (directly or via a linker sequence), and in certain preferred embodiments the Coversin-type protein may comprise or consist of SEQ ID NO:5 or SEQ ID NO:6, or SEQ ID NO:7 or SEQ ID NO:8 e.g. the fusion protein comprises (a) a PAS sequence consisting of 30 copies of SEQ ID NO:13 and (b) (i) SEQ ID NO:5, or (iii) SEQ ID NO:6, or (iii) SEQ ID NO:7, or (iv) SEQ ID NO:8 wherein (a) is fused to the N terminus of (b) directly or via a linker sequence.

In some embodiments the linker comprises one or more alanine residues, e.g. 1-5 alanine residues, e.g. a single alanine residue.

The modified Coversin polypeptides of the invention may be chemically modified, e.g. post-translationally modified. For example, they may be glycosylated, pegylated, phosphorylated or comprise modified amino acid residues. Such modified polypeptides fall within the scope of the term "polypeptide" used herein. In other embodiments the modified Coversin polypeptides of the invention are not chemically modified, e.g. post-translationally modified (e.g. not glycosylated, pegylated, phosphorylated).

Modified Coversin polypeptides of the invention may be in a substantially isolated form. In the case when the polypeptides of the invention have been expressed in a host cell this may be that they have been separated from at least one component of the host cell and/or growth media in which it was expressed. It will be understood that the modified Coversin polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention. This may be determined, for example by electrophoresis or chromatography.

The modified Coversin polypeptides may also be made synthetically or by recombinant means. For example, a recombinant Coversin polypeptide may be produced by transfecting mammalian, fungal, bacterial or insect cells in culture with an expression vector comprising a nucleotide sequence encoding the modified Coversin polypeptide operably linked to suitable control sequences, culturing the cells, extracting and purifying the modified Coversin polypeptide produced by the cells. The polypeptides may also be modified following either synthetic or recombinant production. Polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the modified Coversin polypeptides, provided that the modified Coversin polypeptides retain LK/E binding activity and exhibit reduced or absent complement inhibitor activity (e.g. complement C5 binding activity).

Polynucleotides

According to one aspect of the present invention, polynucleotides encoding the modified Coversin polypeptides of the invention are provided. A polynucleotide encoding a modified Coversin polypeptide or fragment thereof according to the present invention may be used to treat or prevent a disease or condition mediated by leukotrienes or eicosanoids.

In particular, the polynucleotide may comprise or consist of: (a) a coding sequence corresponding to that of SEQ ID NO: 1 (or nucleotides 55 to 507 thereof) with the necessary changes to reflect the modifications made to SEQ ID NO: 2 or SEQ ID NO: 3 in the modified Coversin polypeptides of the invention; (b) a sequence which is degenerate as a result of the genetic code to the sequence as defined in (a); or (c) a fragment of any one of the sequences as defined in (a), or (b) which encodes a modified polypeptide according to the invention having LK/E binding activity (e.g. as described herein in relation to the modified polypeptides) and reduced or absent complement inhibitor activity (e.g. as described herein in relation to the modified polypeptides). Typically the polynucleotide is DNA, e.g. cDNA.

However, the polynucleotide may be a RNA polynucleotide. The polynucleotide may be single or double stranded, and may include within it synthetic or modified nucleotides.

In some embodiments, instead of the coding sequence corresponding to that of SEQ ID NO:1, the coding sequence will correspond to that of nucleotides 55 to 507 of the nucleotide sequence in FIG. 2 (SEQ ID NO: 1). This nucleotide sequence encodes the Coversin protein in FIG. 2 without the signal sequence i.e. encodes SEQ ID NO:3. The first 54 bases of the nucleotide sequence in FIG. 2 encode the signal sequence which is not required for complement inhibitory activity or LTB4 binding activity. The polynucleotides of the invention may thus comprise or consist of modified versions of nucleotides 55 to 507 of the nucleotide sequence in FIG. 2 (SEQ ID NO: 1).

A polynucleotide of the invention can typically hybridize to the coding sequence or the complement of the coding sequence of SEQ ID NO: 1 (or nucleotides 55 to 507 thereof) with the necessary changes to reflect the modifications made to SEQ ID NO: 2 or SEQ ID NO: 3 in the modified Coversin polypeptides of the invention at a level significantly above background. Background hybridization may occur, for example, because of other DNAs present in a DNA library. The signal level generated by the interaction between a polynucleotide of the invention and the coding sequence or complement of the coding sequence of SEQ ID NO: 1 (or nucleotides 55 to 507 thereof) with the necessary changes to reflect the modifications made to SEQ ID NO: 2 or SEQ ID NO: 3 in the modified Coversin polypeptides of the invention is typically at least 10 fold, preferably at least 100 fold, as intense as interactions between other polynucleotides and the coding sequence of SEQ ID NO: 1 (or nucleotides 55 to 507 thereof). The intensity of interaction may be measured, for example, by radiolabelling the probe, e.g. with $^{32}P$. Selective hybridisation may typically be achieved using conditions of medium to high stringency. However, such hybridisation may be carried out under any suitable conditions known in the art (see Sambrook et al, Molecular Cloning: A Laboratory Manual, 1989). For example, if high stringency is required suitable conditions include from 0.1 to 0.2×SSC at 60° C. up to 65° C. If lower stringency is required suitable conditions include 2×SSC at 60° C.

The polynucleotide referred to above may alternatively or additionally be modified to include sequences encoding extension at either or both ends or internally at loop regions of the polypeptide. Additional sequences such as signal sequences may also be included or sequences encoding another peptide or protein to aid detection, expression, separation or purification of the protein or encoding a peptide such as an Fc peptide, PAS or other molecules as referred to elsewhere herein to increase the circulating half-life of the protein, as referred to above. Examples of other fusion partners include beta-galactosidase, glutathione-S-transferase, or luciferase.

The modified polynucleotide generally encodes a polypeptide which has LK/E binding activity. Degenerate substitutions may be made and/or substitutions may be made which would result in a conservative amino acid substitution when the modified sequence is translated, for example as shown in the Table above. A nucleotide sequence which is capable of selectively hybridizing to the complement of the DNA coding sequence of SEQ ID NO: 1 with the necessary changes to reflect the modifications made to SEQ ID NO: 2 or SEQ ID NO: 3 in the modified Coversin polypeptides of the invention will generally have at least 60%, at least 70%, at least 80%, at least 90%, at least 95%, at least 98% or at least 99% sequence identity to the coding sequence of SEQ ID NO: 1 (or nucleotides 55 to 507 thereof) with the necessary changes to reflect the modifications made to SEQ ID NO: 2 or SEQ ID NO: 3 in the modified Coversin polypeptides of the invention over a region of at least 20, preferably at least 30, for instance at least 40, at least 60, at least 100, at least 200, at least 420, or most preferably over the full length of SEQ ID NO: 1 (with the necessary changes to reflect the modifications made to SEQ ID NO: 2 or SEQ ID NO: 3 in the modified Coversin polypeptides of the invention) or the length of SEQ ID NO: 1 (with the necessary changes to reflect the modifications made to SEQ ID NO: 2 or SEQ ID NO: 3 in the modified Coversin polypeptides of the invention) encoding a polypeptide having the sequence shown in SEQ ID NO:2 or 3, subject to the modifications made to these sequences according to the invention). Sequence identity may be determined by any suitable method (as discussed e.g. in Pearson, W. Curr Protoc Bioinformatics. 2013 June; 0 3, doi:10.1002/0471250953.bi0301s42).

Polynucleotides for use in the invention may be produced recombinantly, synthetically, or by any means available to those of skill in the art. They may also be cloned by standard techniques. The polynucleotides are typically provided in isolated and/or purified form.

Polynucleotides as described herein have utility in production of the polypeptides for use in the present invention, which may take place in vitro, in vivo or ex vivo. The polynucleotides may be used as therapeutic agents in their own right or may be involved in recombinant protein synthesis. The polynucleotides for use in the invention are typically incorporated into a recombinant replicable vector. The vector may be used to replicate the nucleic acid in a compatible host cell. Therefore, polynucleotides for use in the invention may be made by introducing a Coversin polynucleotide into a replicable vector, introducing the vector into a compatible host cell and growing the host cell under conditions which bring about replication of the vector. The host cell may, for example, be an *E. coli* cell.

Vectors

The invention also includes cloning and expression vectors comprising the nucleic acid molecules of this aspect of the invention. Such expression vectors may incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Preferably the vector is an expression vector comprising a nucleic acid sequence that encodes a modified Coversin polypeptide as defined herein. The coding sequences may also be selected to provide a preferred codon usage suitable for the host organism to be used. Other suitable vectors would be apparent to persons skilled in the art, see Sambrook et al. (1989). Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

Vectors according to the invention include plasmids and viruses (including both bacteriophage and eukaryotic viruses), as well as other linear or circular DNA carriers, such as those employing transposable elements or homologous recombination technology.

Many such vectors and expression systems are known and documented in the art (Fernandez & Hoeffler, 1998). Particularly suitable viral vectors include baculovirus-, adenovirus- and vaccinia virus-based vectors.

Suitable hosts for recombinant expression include commonly used prokaryotic species, such as *E. coli*, or eukaryotic yeasts that can be made to express high levels of recombinant proteins and that can easily be grown in large quantities. Preferably, the host cell is a eukaryotic yeast cell. Mammalian cell lines grown in vitro are also suitable, particularly when using virus-driven expression systems. Another suitable expression system is the baculovirus expression system that involves the use of insect cells as hosts. An expression system may also constitute host cells that have the DNA incorporated into their genome.

Proteins, or protein fragments may also be expressed in vivo, for example in insect larvae or in mammalian tissues.

A variety of techniques may be used to introduce the vectors according to the present invention into prokaryotic or eukaryotic cells. Suitable transformation or transfection techniques are well described in the literature (Sambrook et al, 1989; Ausubel et al, 1991; Spector, Goldman & Leinwald, 1998). In eukaryotic cells, expression systems may either be transient (e. g. episomal) or permanent (chromosomal integration) according to the needs of the system.

Host Cells

The invention also includes transformed or transfected prokaryotic or eukaryotic host cells comprising a nucleic acid molecule, an antisense nucleic acid molecule or a vector as defined above. Where the host cells are prokaryotic cells, they are preferably *E. coli* cells.

Preferred eukaryotic host cells include eukaryotic yeast cells and mammalian cells.

The invention also provides a method for preparing a modified Coversin polypeptide, as defined above, which comprises culturing a host cell containing a nucleic acid molecule according to the invention under conditions whereby the protein is expressed and recovering the protein thus produced. Preferably, the host cell is a yeast cell or an *E. coli* cell.

Compositions

According to a further aspect of the invention there is provided a composition comprising a modified Coversin polypeptide, a fusion protein comprising a modified Coversin polypeptide, or a nucleic acid molecule comprising a nucleic acid sequence encoding a modified Coversin polypeptide, according to the above-described aspects of the invention, in conjunction with a pharmaceutically acceptable carrier.

The term "pharmaceutically acceptable carrier", as used herein, includes genes, polypeptides, antibodies, liposomes, polysaccharides, polylactic acids, polyglycolic acids and inactive virus particles or indeed any other agent provided that the excipient does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. By way of example a solution in water or PBS may be used.

Excipients may enable the pharmaceutical compositions to be formulated into tablets, pills (including mechanical pills), dragees, capsules, liquids, gels, syrups, slurries, suspensions, emulsions, ointments, creams, aerosol sprays, to aid intake by the patient. Nanoparticles for the delivery of therapeutic substances or iontophoresis may also be used. A thorough discussion of pharmaceutically acceptable carriers is available in Remington's Pharmaceutical Sciences (Mack Pub. Co., N. J. 1991).

According to a further aspect, the present invention provides a modified Coversin polypeptide, a fusion protein comprising a modified Coversin polypeptide, or a nucleic acid molecule comprising a nucleic acid sequence encoding a modified Coversin polypeptide, according to the above-described aspects of the invention, for use in therapy.

The invention also provides a method of treating an animal suffering from a LK/E (in particular $LTB_4$) mediated disease or disorder or preventing an animal developing a LK/E (in particular $LTB_4$) mediated disease or disorder comprising administering to said animal a modified Coversin polypeptide, a fusion protein comprising a modified Coversin polypeptide, or a nucleic acid molecule comprising a nucleic acid sequence encoding a modified Coversin polypeptide, according to the above-described aspects of the invention, or a pharmaceutical composition according to the above-described aspects of the invention in a therapeutically or prophylactically effective amount.

The invention also provides a modified Coversin polypeptide, a fusion protein comprising a modified Coversin polypeptide, or a nucleic acid molecule comprising a nucleic acid sequence encoding a modified Coversin polypeptide, according to the above-described aspects of the invention, for use in a method of treating an animal suffering from a LK/E (in particular $LTB_4$) mediated disease or disorder or preventing an animal developing a LK/E (in particular $LTB_4$) mediated disease or disorder.

Preferably, said animal is a mammal, more preferably a human.

The term "therapeutically effective amount" refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy.

The precise amount can be determined by routine experimentation, but may ultimately lie with the judgement of the clinician. Preferably, the dose of the agent is sufficient to bind as much available LK/E e.g. $LTB_4$ as possible in the subject, more preferably, all available LK/E e.g. $LTB_4$.

The frequency with which the dose needs to be administered will depend on the half-life of the agent involved. The modified Coversin polypeptide, may be administered as a continuous infusion, in bolus doses or on a daily basis, twice daily basis, or every two, three, four days, five, six, seven, 10, 15 or 20 days or more. A particular advantage of the modified Coversin polypeptides is the relative ease and rapidity with which they can be administered, and the fact that medical professionals are not required to administer the protein.

Single or multiple doses may be administered. For example at least 2, 3, 4, 5, 6, 7, or 8 doses may be administered. Single doses are one embodiment. The exact dosage and the frequency of doses may also be dependent on the patient's status at the time of administration. Factors that may be taken into consideration when determining dosage include the need for treatment or prophylaxis, the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician.

The dosage regimen may also take the form of an initial "loading dose" followed by one or more subsequent "maintenance doses". In general, the loading dose will be greater than the maintenance dose. The loading dose may be 2, 5, 10 or more times greater than the maintenance dose. The loading dose may be administered as a single dose, or as one or more doses in a particular time frame. Typically, the loading dose will be 1, 2, 3, 4 or 5 doses administered in a single 24 hour period. The maintenance dose may be a lower dose that is repeated at regular intervals. The maintenance dose may be repeated at intervals, such as every 3, 4, 6, 8, 12, 24, or 48 hours. The precise regimen can be determined by routine experimentation, but may ultimately lie with the judgement of the clinician. The maintenance dose may be at least 20, 30, 40, 50, 60, 70, 80, 90 or 100% of the initial loading dose, or up to 20, 30, 40, 50, 60, 70, 80, 90 or 100% of the initial loading dose.

In a further embodiment the same dose is used throughout the course of treatment (e.g. daily).

The modified Coversin polypeptide, a fusion protein comprising a modified Coversin polypeptide, or a nucleic acid molecule comprising a nucleic acid sequence encoding a modified Coversin polypeptide or may be delivered by any known route of administration. It may be delivered locally or systemically. It may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays. Local administration may include topical administration. Preferably it is delivered via subcutaneous injection.

Diseases and Conditions

The present inventors have found that modified Coversin polypeptides as defined in the present application and claims have the ability to bind to E/LK, e.g. $LTB_4$, but show no or reduced C5 binding. $LTB_4$ is the most powerful chemotatic and chemokinetic eicosanoid described and promotes adhesion of neutrophils to the vascular endothelium via up-regulation of integrins. $LTB_4$ induces aggregation of neutrophils and through a variety of processes plays a role in inflammation. $LTB_4$ has been shown to have roles in the induction and management of adaptive immune responses. Thus, the modified Coversin polypeptides, having the ability to bind to and cage leukotrienes and hydroxyeicosanoids can prevent these ligands interacting with BLT1 and BLT2 receptors and can be used to ameliorate the proinflammatory effects of the fatty acids.

Examples of diseases and disorders which can be treated using modified Coversin polypeptides of the present invention are set out below.

Alpha-1 antitrypsin disease (AATD), pulmonary arterial hypertension (PAH), chronic obstructive pulmonary disease (COPD), bronchiolitis obliterans syndrome (BOS), idiopathic pulmonary disease (IPD), severe persistent asthma, exercise and aspirin induced asthma, allergic rhinitis, silicosis.

Autoimmune blistering diseases, atopic dermatitis, contact dermatitis, psoriasis, Churg-Strauss Syndrome.

Rheumatoid arthritis, osteoclastic arthritis, post-menopausal osteoporosis, systemic lupus eyrthematosus (SLE), inflammatory bowel disease, vasculitides including Goodpasture's Syndrome and glomerulonephritis, systemic sclerosis, type 2 diabetes, diabetic nephropathy, sickle cell disease (SCD), malaria, trauma, myocardial infarction, obstructive sleep apnea syndrome, atherosclerosis, restenosis after coronary angioplasty, multiple sclerosis (MS), neuropathy.

Pancreatic cancer, ovarian cancer, colon cancer, prostate cancer, lung cancer, oesophageal cancer, cancer metastases.

Sjogren's dry eye, Graft versus host syndrome dry eye, Keratoconjunctivitis sicca, Atopic keratoconjunctivitis, mucuous membrane pemphigoid, Vernal keratoconjunctivitis, Blepharo keratoconjunctivitis, Perennial keratoconjunctivitis, Ocular lupus erythematosus, Ocular rosacea, Trachoma, Bacterial, viral or fungal keratitis, Ocular herpes simplex or herpes zoster, Keratoconus including but not limited to the following varieties: Hereditary, Traumatic, Retinitis pigmentosa, Retinitis of prematurity, Down's syndrome, Osteogenesis imperfecta, Addison's disease, Leber's congenital amaurosis, and Ehlers-Danlos syndrome, Map-dot-fingerprint corneal dystrophy, Fuch's corneal dystrophy, Lattice corneal dystrophy, Photokeratitis, Anterior uveitis, Pterygium, autoimmune uveitis, allergic conjunctivitis.

Examples of some specific disorders that can be treated in accordance with the present invention include uveitis, atopic dermatitis, contact hypersensitivity, ulcerative colitis, oesophygeal adenocarcinoma, pancreatic adenocarcinoma, breast cancer, ovarian cancer, colon cancer, lung cancer, acne, obliterative bronchiolitis, aneurysms, periodontal disease, cystic fibrosis, prostate cancer, post-inflammatory pigmentation, fibromyalgia, systemic lupus erythematosus, tumor metastasis, sclerodermia, multiple sclerosis, sarcoidosis, radiation induced gastrointestinal inflammation, and gout.

Further conditions and disorders that can be treated in accordance with the present invention include asthma, bronchitis, atherosclerosis, psoriasis, psoriatic arthritis, inflammatory bowel disease (including Crohn's disease), sepsis, arteritis, myocardial infarction, stroke, and coronary heart disease, ischaemia reperfusion injury, nephritis and arthritis, including rheumatoid arthritis, spondyloarthropathies, osteoarthritis, and juvenile arthritis. Conditions known to be mediated by $LTB_4$ that can be treated in accordance with the present invention include obliterative bronchiolitis, scleroderma interstitial lung disease, periodontal disease, chronic B lymphocytic leukaemia, prostate cancer and atherosclerosis. Conditions known to be mediated by $LTB_4$ and complement that can be treated in accordance with the present invention include nephritis, arthritis of various sorts, uveitis, cancer, sepsis, ischaemia reperfusion injury, stroke and myocardial infarction.

Most preferably the invention is used in the treatment of AATD, COPD, PAH, severe persistent asthma, GVHD, blistering skin diseases and psoriasis.

Complement and LK/E Activity

The modified Coversin polypeptides of the invention exhibit leukotriene or hydroxyeicosanoid binding activity. As a result of the modifications to the amino acid sequence in SEQ ID NO: 2 or 3, the modified Coversin polypeptides also exhibit reduced or absent complement C5 binding activity (relative to the unmodified Coversin amino acid sequence in SEQ ID NO: 2 or SEQ ID NO: 3).

Reduced/Absent C5 Binding

The ability of a modified polypeptide of the invention to bind to the complement C5 protein, including C5 from subjects with C5 polymorphisms, may be determined by standard in vitro assays known in the art, for example by western blotting following incubation of the protein on the gel with labelled C5 or surface plasmon resonance (see, for example Example 2).

Wild type Coversin binds to C5 and prevents its cleavage by C5 convertase in rat, mouse and human serum with an $IC_{50}$ of approximately 0.02 mg/ml. The Coversin protein has been demonstrated to bind to C5 with a $K_D$ of 1 nM, determined using surface plasmon resonance (SPR) (see, for example Example 2).

The modified Coversin polypeptides will preferably exhibit a reduced ability to bind to C5 compared to the unmodified Coversin polypeptide. In preferred embodiments, the modified Coversin polypeptides may exhibit no detectable binding to C5.

In some embodiments of the invention C5 binding is, for example, reduced by at least 2, 5, 10, 15, 20, 50, 100 fold, or eliminated relative to the binding exhibited by the unmodified Coversin polypeptide in SEQ ID NO: 2 or 3.

In some embodiments C5 binding is reduced by at least 50%, 60%, 70%, 80%, 90% or 95% relative to the unmodified Coversin polypeptide in SEQ ID NO: 2 or 3.

In some embodiments, the modified Coversin polypeptides bind C5 with a $K_D$ greater than 1 micromolar as determined by Surface Plasma Resonance according to the method described in Roversi et al. (2013) J Biol Chem. 288, 18789-18802, or as set out in Example 2.

In some embodiments, the modified Coversin polypeptides inhibit sheep red blood cell lysis by less than 10% when present at a concentration of 0.02 mg/mL in whole pooled normal serum with the CH50 lytic assay performed according to or similarly to Giclas 1994.

The ability of the modified polypeptide of the invention to bind to C5 may be determined by measuring the ability of the agent to inhibit complement activation in serum. For example, complement activity in the serum can be measured by any means known in the art.

Unaffected LK/E Binding

The modified Coversin polypeptide of the invention may inhibit LK/E (e.g. leukotriene B4 ($LTB_4$)) activity. In particular, the modified Coversin polypeptide of the invention may bind such molecules. The ability of an agent to bind these molecules may be determined by standard in vitro assays known in the art, for example by means of a competitive ELISA between Coversin and an anti LK/E (e.g. anti-$LTB_4$) antibody competing for binding to labelled LK/E (e.g. $LTB_4$). Such an assay is set out in Roversi et al 2013.

The modified Coversin polypeptide according to the invention may bind LK/E with the same or greater affinity as wild type Coversin. Some reduction in binding may also be acceptable.

Coversin LTB4 binding may also be expressed in terms of the $K_D$, as determined by fluorescence titration. Data obtained using fluorescence titration has shown that wild type Coversin binds $LTB_4$ with a $K_D$ of between 200-300 pM. Modified Coversin polypeptides according to the invention will preferably bind $LTB_4$ with a $K_D$ of less than 5 nM, 2 nM, or 1 nM, more conveniently less than 0.9 nM, most conveniently less than 0.8 nM, preferably less than 0.7 nM, more preferably less than 0.6 nM, preferably less than 0.5 nM, even more preferably less than 0.4 nM, and advantageously less than 0.3 nM, wherein said $K_D$ is determined using fluorescence titration, e.g. according to the method described in Example 3.

In some embodiments, the modified Coversin polypeptides compete with antibody for binding to $LTB_4$ according to the ELISA methodology described in Roversi et al. (2013) J Biol Chem. 288, 18789-18802.

EXAMPLES

Example 1: Expression of Coversin Variants in *E. coli*

Genetic constructs encoding Coversin variants 1 (SEQ ID NO: 5) and 2 (SEQ ID NO: 6) were cloned into *E. coli* expression vectors which were then transformed into an *E. coli* expression strain. Fermentations of the bacterial cultures were then performed with complex medium using an established fermentation protocol.

The resulting clarified cell culture was concentrated in 20 mM Bis-Tris buffer, pH 6.0, and applied to a DEAE-Sepharose FF column (GE Healthcare) and then eluted with a step gradient of NaCl in the same buffer. Purified fractions were then run on a Phenyl Sepharose HP column using a linear gradient of $(NH_4)_2SO_4$ in 20 mM Bis-Tris buffer. Chromatography fractions were analysed with SDS-PAGE and pooled. For Coversin variant 1, a further purification step was carried out where the pooled protein fractions were applied to a Superdex 75 gel filtration column. For Coversin variant 2, a further purification step was carried out where pooled protein fractions were applied to a Q-sepharose ion exchange column.

Figure 3:
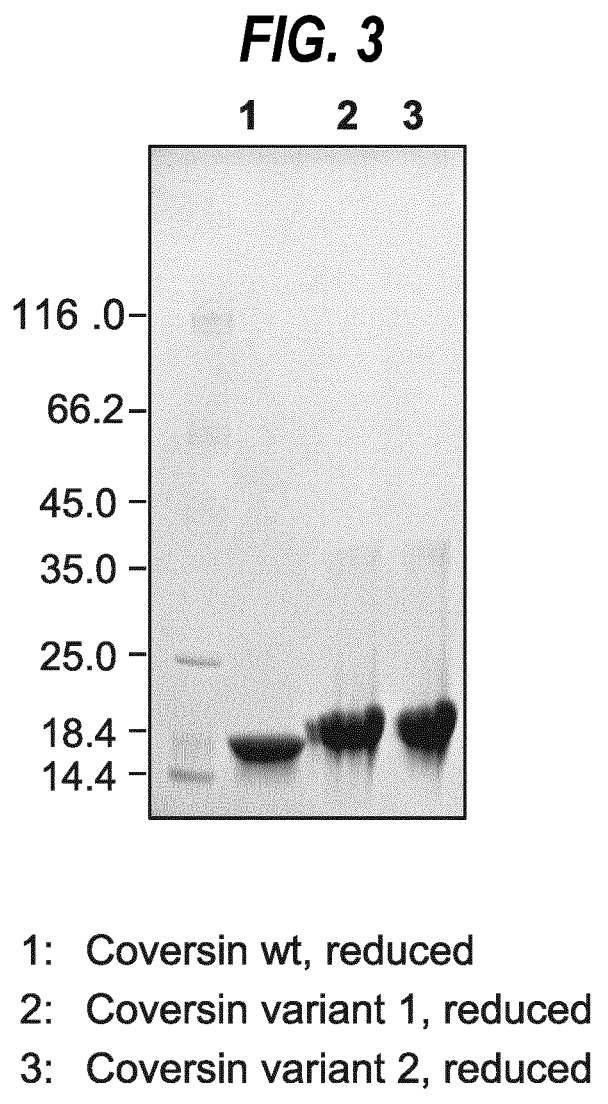

Purified fractions of variants 1 and 2 were then run on an SDS-PAGE gel alongside wild type Coversin. The results are shown in FIG. 3 and demonstrate that both Coversin variants express well in *E. coli.*

Example 2: Coversin Variants 1 and 2 Lose C5 Binding Activity Relative to Wild Type Coversin In order to measure binding activity of wild type Coversin to C5 relative to the binding activity of Coversin variants 1 and 2, SPR experiments were carried out using a Biacore instrument (GE Healthcare). HEPES-Buffered Saline with 0.05% Tween 20 was used as the running buffer at a flow rate of 30 μl/min and human C5 was immobilised on a CM3 sensor chip to a total of 4800 RU.

Real-time affinity measurements were performed at 25° C. on a BIAcore 2000 system (GE Healthcare, Munich, Germany). Human C5 (Complement Technology, Tyler, Tex., USA) was initially immobilized in 10 mM Na-acetate pH 5.0 at a concentration of 25 μg/mL on a CM3 sensorchip (GE Healthcare) using an amine coupling kit (GE Healthcare), resulting in a ligand density of 4200-4800 resonance units (RU). Purified Coversin, variant 2 and variant 1 were injected either in a dilution series (0-96 nM for Coversin) or at 1 μM in the case of the variants, in the presence of HEPES-buffered saline (HBS; 10 mM HEPES/NaOH pH 7.4, 150 mM NaCl) containing 0.05% v/v Tween 20 as running buffer (HBST-0.05). Complex formation was observed at a continuous flow rate of 30 μl/min over 240 s. Subsequently, dissociation was allowed to proceed for 900 s before regenerating with 8 μl ImmunoPure Gentle Ag/Ab elution buffer (ThermoFisher Scientific, Waltham, Mass., USA) to disrupt the strong electrostatic interaction between Coversin and C5, followed by the injection of 120 μl HBST-0.05 containing 1 mM EDTA and 120 μl HBST-0.05 to clean the flow-cell. The sensorgrams were corrected by double subtraction of the corresponding signals measured for the in-line control blank channel and an averaged baseline determined from three buffer blank injections as previously described (Myszka D. G. (1999) Improving biosensor analysis. J Mol Recognit. 12(5):279-284). The kinetic parameters were determined using BIAevaluation software by global fitting the data to a Langmuir binding model for bimolecular complex formation.

Figure 4A:
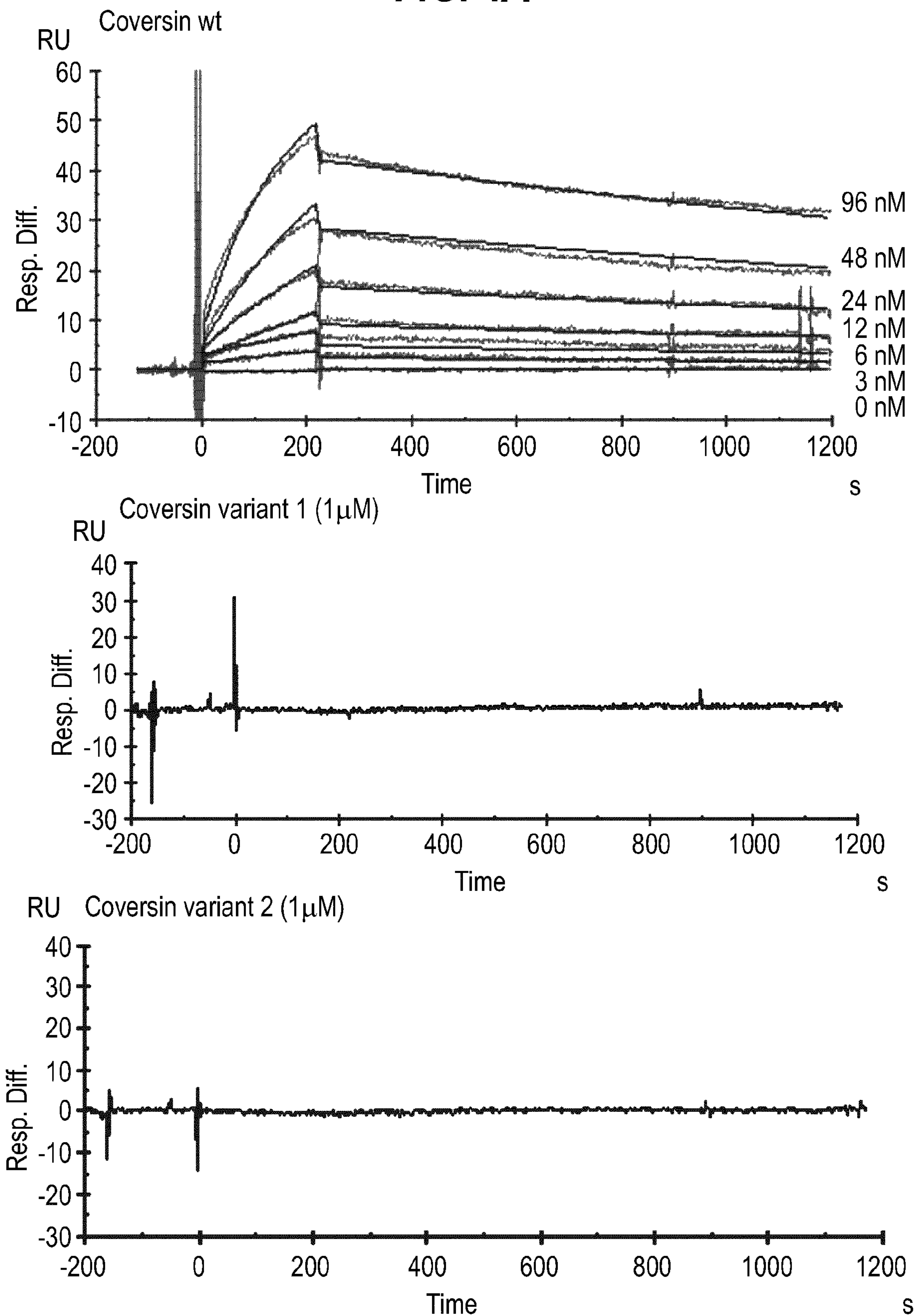
FIG. 4 shows surface plasmon resonance traces for wild type Coversin and Coversin variants 1 and 2 binding to C5 (A) as well as PASylated versions thereof (B).

As shown in FIG. 4*a*, Coversin bound to the immobilised C5 with a $K_D$ of 1.45 nM. By contrast, when the same experiment was carried out with a single measurement of Coversin variants 1 and 2 at 1 μM, neither produced a significant response, demonstrating that neither of the variants bind to C5. PASylated versions of Coversin variants 1 and 2 were also tested and gave similar results (FIG. 4B).

Example 3: Coversin/Variants Bind $LTB_4$ in the Picomolar Range

Fluorescence titration of Coversin binding to $LTB_4$ was carried out for wild type Coversin and variants 1 and 2 as well as the PASylated versions thereof.

Binding activity of Coversin, and variants 1 and 2 and the PASylated versions thereof for $LTB_4$ (Caymen Chemicals, Ann Arbor, Mich., USA) in phosphate buffered saline (PBS) was quantified in a LS 50 B spectrofluorimeter (Perkin-Elmer, Norwalk, Conn., USA). Purified 100 nM solutions of the proteins in 2 mL PBS were applied in a quartz cuvette (10 mm path length; Hellma, Mühlheim, Germany) equipped with a magnetic stirrer. Temperature was adjusted to 20° C. and, after equilibrium was reached, protein Tyr/Trp fluorescence was excited at 280 nm (slit width: 15 nm). The fluorescence emission was measured at 340 nm (slit width: 16 nm) corresponding to the emission maximum. A ligand solution of 30 μM $LTB_4$ in PBS was added step-wise, up to a maximal volume of 20 μL (1% of the whole sample volume), and after 30 s incubation steady state fluorescence was measured. For calculation of the $K_D$ value, data was normalized to an initial fluorescence intensity of 100%, the inner filter effect was corrected using a titration of 3 μM N-acetyl-tryptophanamide solution and data was plotted against the corresponding ligand concentration. Then, non-linear least squares regression based on the law of mass action for bimolecular complex formation was used to fit the data with Origin software version 8.5 (OriginLab, Northampton, Mass., USA) using a published formula (Breustedt et al., 2006 Comparative ligand-binding analysis of ten human lipocalins. Biochim Biophys Acta 1764(2): 161-173).

FIGS. 5A and B show that both Coversin variants as well as the PASylated versions thereof retain $LTB_4$ binding activity, binding $LTB_4$ with a $K_D$ in the picomolar range.

Example 4: Analysis of Thermal Stability Using CD Spectroscopy

Circular dichroism was used to detect protein unfolding as a result of thermal denaturation. Using this method, the melting temperature of wild type Coversin and Coversin variants 1 and 2 was obtained.

Thermal unfolding of was measured in a J-810 spectropolarimeter (Jasco, Tokyo, Japan) equipped with a Peltier element PT-423S, both controlled by the Spectra Manager version 1.53.05 instrument software. Protein solutions were buffer-exchanged to 20 mM $KP_i$ pH 7.5, 50 mM $K_2SO_4$ via dialysis overnight at 4° C. using a Slide-A-Lyzer™ mini dialysis device (ThermoFisher Scientific, Waltham, Mass., USA) and spectra were recorded at a protein concentration of 12.5 μM in a quartz cuvette (1 mm path length; Hellma) at 20° C. and at 94° C. from 190 nm to 250 nm. In this way the optimal signal change for the denaturation studies was identified at 217 nm. Melting temperatures ($T_m$) were determined with protein solutions upon heating from 20° C. to 94° C. at a gradient of 60 K/h. Data were recorded at 217 nm and evaluated according to the two-state-model of protein folding using a published formula (Schlehuber and Skerra, 2002 Tuning ligand affinity, specificity, and folding stability of an engineered lipocalin variant—a so-called 'anticalin'—using a molecular random approach. Biophys Chem. 96(2-3):213-228) with KaleidaGraph software (Synergy software, Reading, Pa., USA).

The fraction of unfolded protein was plotted against temperature to give the melting curves in FIG. 6 and a value for the melting temperature of wild type Coversin and variants 1 and 2. As shown in FIG. 6, wild type Coversin has a melting temperature of 61.06° C.±0.03° C., variant 2 has a melting temperature of 57.83° C.±0.04° C., and variant 1 has a melting temperature of 50.16° C.±0.06° C.

Examples 5: Coversin Variants Demonstrate No C5 Inhibitory Activity

In order to assess the inhibitory effects of Coversin/Coversin variants 1 and 2 on C5, a CH50 assay was carried out with purified Coversin proteins using the protocol detailed below.

Sheep red blood cells (SRBCs) were sensitised using rabbit hemolysin (Sigma) according to the method of Giclas et al. 1994. Assays were conducted in a total volume of 50 μl using 25 μl pooled normal human sera (NHS) diluted 1:80 in gelatin veronal buffered saline supplemented with calcium and magnesium and 25 μl of sensitised SRBCs. All lytic assays were set up on ice. Serial dilutions of Coversin, Coversin variant 1 and Coversin variant 2 were made up in the diluted NHS. Assays were incubated for 30 minutes at 37° C. with shaking at 350 rpm. Reactions were stopped by micro centrifugation at 4000 g for 5 seconds and supernatant removed to a flat bottomed 96 well plate. 100 μl ddH2O was added to each well and percentage lysis in the presence of the proteins calculated as a percentage of total lysis induced by adding 25 μl of water to the reactions in place of the diluted NHS.

The inhibitory effect of each protein on C5 was assessed through the percentage lysis of cells in the presence of each of the Coversin proteins. Absorbance measurements were taken as a measure of cell lysis at 405 nm along the range of Coversin protein concentrations.

FIG. 7 shows that the percentage of cell lysis in the samples containing different concentrations of wild type Coversin was maintained below 10% at each concentration, demonstrating the known inhibitory effect of C5 by wild type Coversin. In contrast, nearly all of the cells in the samples containing both Coversin variants at different concentrations were lysed, indicating that neither of the variants possess any detectable inhibitory activity towards C5.

Example 6: L-Coversin Reduces Granulocyte Infiltrate in HDM Mouse Models of Asthma To test the effect of Coversin variants in vivo, variant 2 was introduced to a mouse model of asthma, induced by a house dust mite (HDM) allergen (see Gregory, L. G., et al., 2009). The Six groups of mice were tested as outlined below:

1. PBS (n=4)
2. L-Coversin (n=4)
3. HDM (n=6)
4. HDM/L-Coversin (n=6)

25 μg of HDM was administered intra tracheally (i.t.) to groups of 4-6 mice in 50 μl PBS 3 times per week for 3 weeks. 100 μg of L-Coversin was administered in 50 μl PBS daily for 3 weeks. PBS was administered in the same dosing regimen to the control (group 1).

Figure 8:
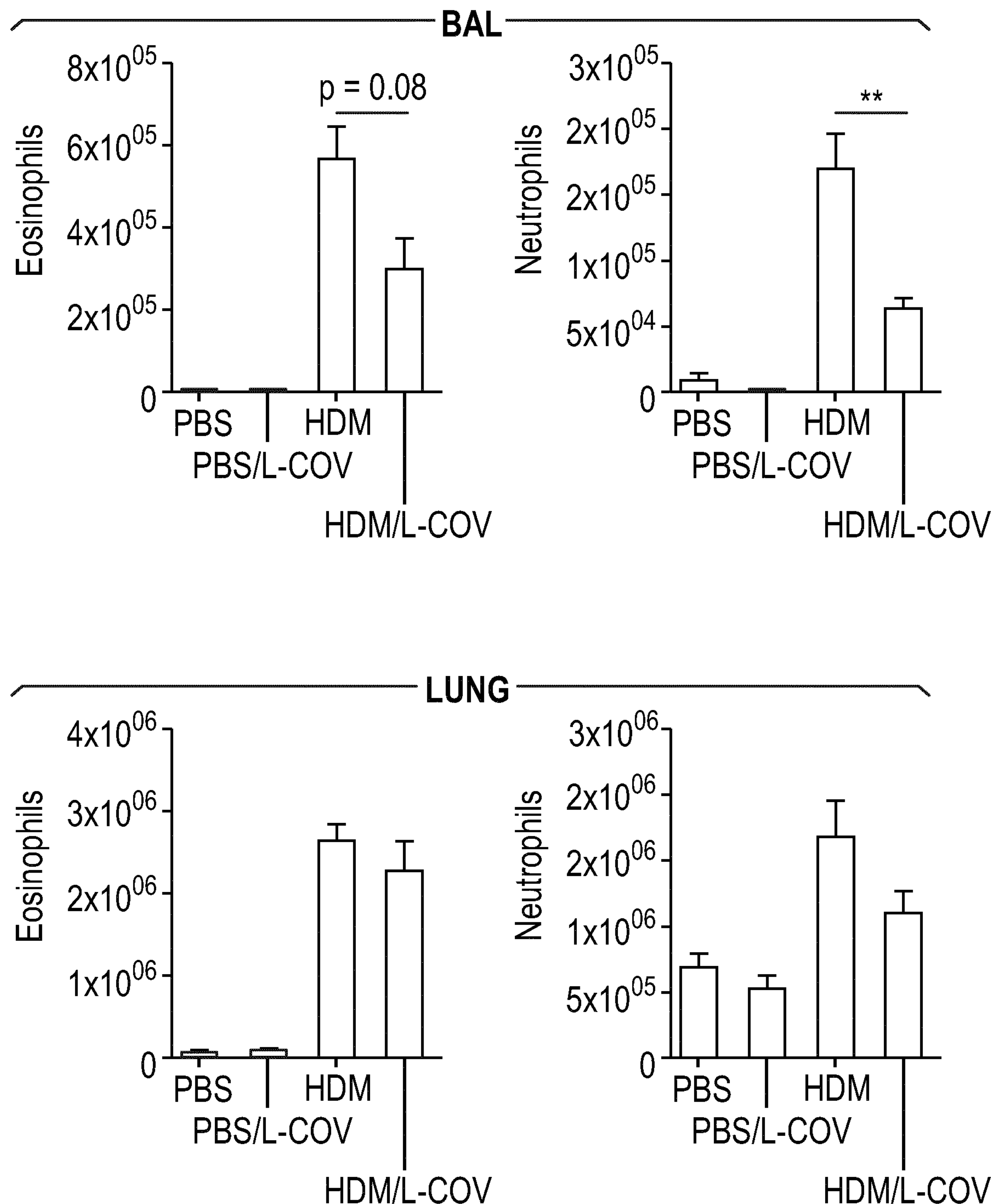
FIG. 8 shows the effect of L-Coversin on eosinophil and neutrophil number in the broncho alveolar fluid and lungs of mouse models of asthma. Asthmatic mice were exposed to house dust mite (HDM) prior to administration of L-Coversin. Phosphate-buffered saline was introduced to control groups of mice in place of HDM exposure.

The levels of eosinophils and neutrophils in the broncho alveolar lavage fluid (BALF) were then tested for each group. The results are shown in FIG. 8. It is shown in FIG. 8 that L-Coversin causes a significant reduction in neutrophil numbers and a near significant reduction in eosinophil numbers in the broncho alveolar lavage fluid relative to the HDM-only control.

Example 7: PASylated L-Coversin in EBA Transfer Model

Antibody transfer epidermolysis bullosa acquista (EBA) was induced using a modified version of the protocol described by Sitaru et al., 2005. Briefly, mice were injected subcutaneously with 50 μg affinity-purified anti-Col7 IgG on days 0, 2, and 4. Mice were injected subcutaneously twice daily with Coversin or PASylated L-Coversin (PASylated variant 2) starting four days before the first injection of anti-Col7 IgG (day −2). This application was continued throughout the experiment until its last day on day 11. In the control groups the mice received only the vehicle subcutaneously.

To generate antibodies directed to murine type VII collagen ("anti-COL7"), New Zealand White rabbits were immunized with 200 μg of a protein mixture containing three different recombinant proteins ("Col7A, B, and C") derived from the non-collagenous 1 (NC1) domain of collagen VII together with incomplete Freund's adjuvant. IgGs were isolated from the serum of immunized rabbits by use of protein G, and afterwards IgGs were affinity-purified with his-Col7 to specifically obtain rabbit anti-Col7 IgG. Antibodies were quality checked by determining the titer and the potency in the cryosection assay.

Starting on day 4, the extent of skin lesions was scored in each individual mouse every other day. Skin areas exhibiting erythema, blisters, erosions, crusts, or alopecia were categorized as "affected" or "unaffected" by a trained observer [Sitaru et al., 2005]. The percentage of the total body surface affected by skin lesions (ABSA) was calculated.

Figure 9A:
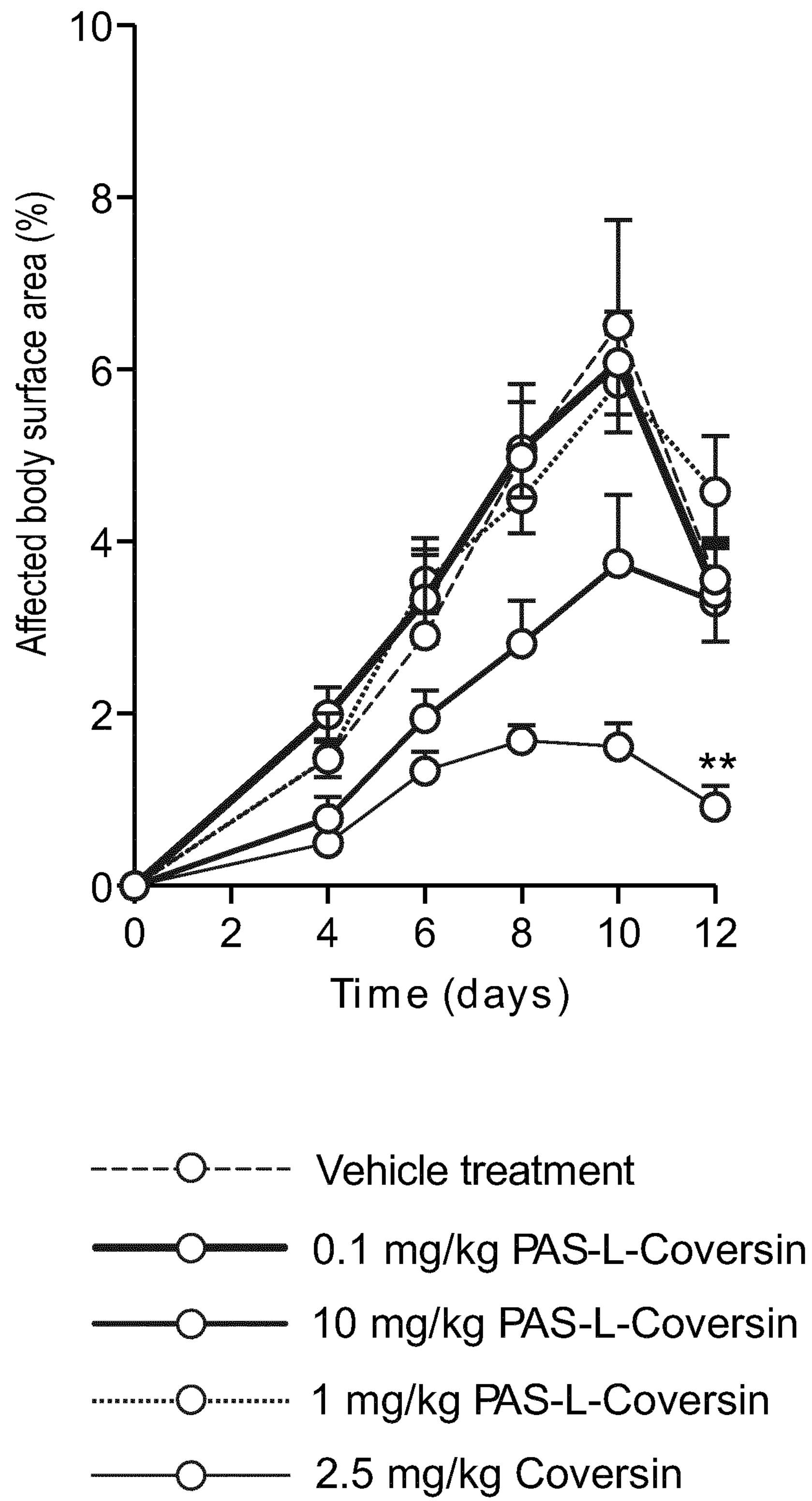
FIG. 9 shows the effect of long acting L-Coversin (PAS-L-Coversin) on mouse model of EBA (A—experiment 1, B experiment 2).
Figure 9B:
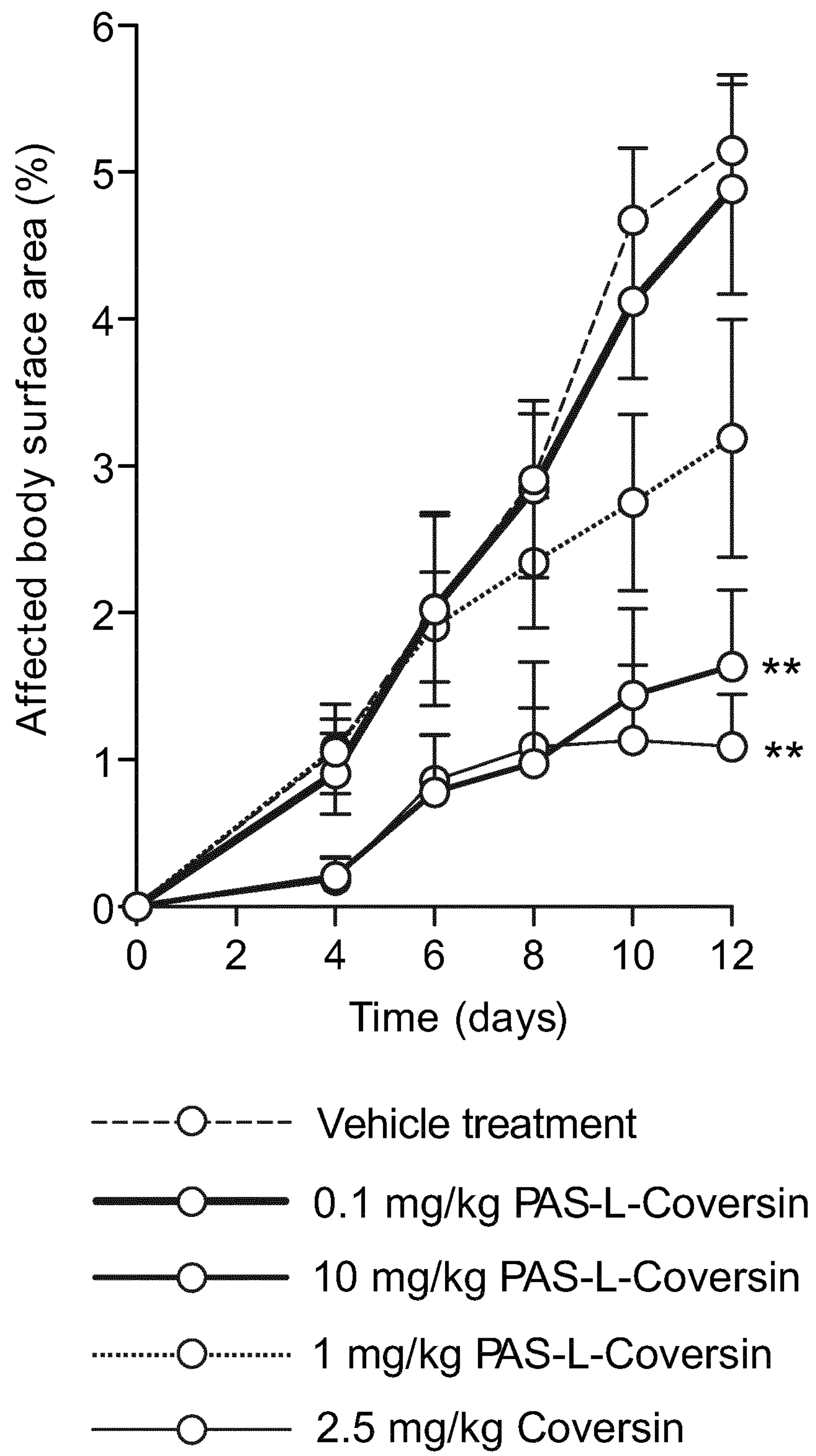

The results of the experiment are shown in FIG. 9. It can be seen that the percentage ABSA in mice treated with Coversin at 2.5 mg/kg was reduced, and that ABSA in mice treated with PASylated L-Coversin variant 2 at 10 mg/kg was also reduced. The PAS-L-Coversin sequence used was variant 2 with a PAS sequence fused to the N-terminus. Because of the higher molecule weight of the PAS-L-Cov, 10 mg/kg PAS-L-Cov corresponds to 2.5 mg/kg Coversin.

REFERENCES

Aya, I. (2006) Blockade of leukotriene B4 signalling pathway directly inhibits cell proliferation and induces apoptosis colon cancer, Yokohama Medical Journal 57, 43-52.

Ausubel, F. M., Davis, K. R., Schott, E. J., Dong, X., and Mindrinos, M. (1991) Identification of signal transduction pathways leading to the expression of *Arabidopsis thaliana* defense genes, Advances in Molecular Genetics of Plant-Microbe Interactions 1: 357-364.

Barratt-Due, A., Thorgersen, E. B., Lindstad, J. K., Pharo, A., Lissina, O., Lambris, J. D., Nunn, M. A., Mollnes, T. E. (2011) *Ornithodoros moubata* complement inhibitor is an equally effective C5 inhibitor in pigs and humans. J Immunol. 187(9):4913-9

Bisgaard H., Groth S., and Madsen F. (1985). Bronchial hyperreactivity to leukotriene D4 and histamine in exogenous asthma. Br Med J. 290, 1468-1471.

Chen, M., Lam, B. K., Kanaoka, Y., Nigrovic, P. A., Audoly, L. P., Austen, K. F. and Lee D. M. (2006). Neutrophil derived leukotriene B4 is required for inflammatory arthritis. J. Exp. Med. 203, 837-842.

Curry, S. L., Cogar, S. M. and Cook, J. L. (2005). Nonsteroidal Antiinflammatory Drugs: A Review. Journal of the American Animal Hospital Association 41, 298-309.

Curtis-Prior, P. (ed.) The Eicosanoids. John Wiley & Sons. ISBN 0471 1489840.

Czarnetzki, B. (1983). Increased monocyte chemotaxis towards leukotriene B4 and platelet activating factor in patients with inflammatory dermatoses. Clin Exp Immunol. 54, 486-492.

Del Prete A., Shao W. H., Mitola S., Santoro G., Sozzani S., and Haribabu, B. (2007) Regulation of dendritic cell migration and adaptive immune response by leukotriene B4 receptors: a role for LTB4 in up-regulation of CCR7 expression and function. Blood, 109, 626-631.

Drazen J. M. (1988). Comparative contractile responses to sulfidopeptide leukotrienes in normal and asthmatic human subjects. Ann NY Acad Sci. 524, 289-297.

Dube L. M., Swanson L. J., Awni W. M., Bell R. L., Carter G. W., Ochs R. F. (1998). Zileuton: the first leukotriene inhibitor for use in the management of chronic asthma. In: Drazen J M, Dahlen S, Lee T H, eds. Five-lipoxygenase Products in Asthma. New York, N.Y.: Marcel Dekkar, Inc.

Fernandez, J., and Hoeffler, J. Gene Expression System: Using Nature for the Art of Expression, 1998

Ford-Hutchinson, A. (1990). Leukotriene B4 in inflammation. Crit. Rev. Immunol. 10, 1-12.

Giclas, P. C. (1994). Classical and alternative pathway evaluation (sections 13.1 and 13.2). In Current Protocols in Immunology, Vol. 3, Complement. Editors: J. E. Coligan, A. M. Kruisbeek, D. H. Margulies, E. M. Shevach and W. Strober. Series editor: R. Coico. John Wiley and Sons, Inc., USA.

Gregory, L. G., et al., Inhaled house dust mite induces pulmonary T helper 2 cytokine production. Clin Exp Allergy, 2009. 39(10): p. 1597-610.

Hao C M. and Breyer M. D. (2007). Physiologic and pathophysiologic roles of lipid mediators in the kidney. Kidney International 71, 1105-1115.

Harrison, K. A., Murphy, R. C. (1995). Isoleukotrienes are biologically active free radical products of lipid peroxidation. J. Biol. Chem. 270, 17273-17276.

Hepburn, N. J., Williams, A. S., Nunn, M. A., Chamberlain-Banoub, J. C, Hamer, J., Morgan, B. P. and Harris, C L. (2007) In vivo characterisation and therapeutic efficacy of C5-specific inhibitor from the soft tick *Ornithodoros moubata*. J Biol Chem. 282, 8292-8299.

Hoover, H., Karnovasky, M., Austen, K., Corey, E. and Lewis, R. (1984). Leukotriene B4 action on endothelium mediates augmented neutrophil/endothelial adhesion. Proc. Nat. Acad. Sci. U.S.A. 81, 2191-2193.

Imig, J. D. (2000). Eicosanoid regulation of the renal vasculature. Am. J. Physiol. Renal Physiol. 279, F965-F981.

Jore, M. M. et al (2016) Structural basis for therapeutic inhibition of complement C5, Nature Structural & Molecular Biology 23, 378-386

Klaas P J. M. van Gisbergen, Marta Sanchez-Hernandez, Teunis B. H. Geijtenbeek, and Yvette van Kooyk (2005) Neutrophils mediate immune modulation of dendritic cells through glycosylation-dependent interactions between Mac-1 and DC-SIGN. J. Exp. Med. 201, 1281-1292.

Kim, N. D., Chou, R. C., Seung, E., Tager, A. M. and Luster, A. D. (2006). A unique requirement for the leukotriene B4 receptor BLTI for neutrophil recruitment in inflammatory arthritis. J. Exp. Med. 203, 829-835.

Kim, N. D. and Luster, A. D. (2007) Regulation of immune cells by eicosanoid receptors, The Scientific World Journal 7, 1307-1328.

Lundeen K. A., Sun B., Karlsson L., and Fourie A. M. (2006) Leukotriene B4 receptors BLTI and BLT2: expression and function in human and murine mast cells. J. Immunol. 177, 3439-3447.

Miyahara, N., Miyahara, S., Takeda, K., and Gelfand G. W. (2006). Role of the LTB4/BLT1 Pathway in Allergen-induced Airway Hyperresponsiveness and Inflammation. A llergol Int. 55, 91-7.

Noiri, E., Yokomizo, T., Kakao, A., Izumi, T., Fujita, T., Kimura, S., and Shimizu, T. (2000). An in vivo approach showing the chemotactic activity of leukotriene B(4) in acute renal ischaemic-reperfusion injury. Proc Nat Acad Sci USA 97, 823-828.

Nunn, M. A., Sharma, A., Paesen, G. C., Adamson, S., Lissina, O., Willis, A. C., & Nuttall, P. A. (2005) Complement inhibitor of C5 activation from the soft tick *Ornithodoros moubata* J. Immunol. 174, 2084-2091. Paesen G C, Adams P L, Harlos K, Nuttall P A, Stuart D I. (1999) Tick histamine-binding proteins: isolation, cloning, and three-dimensional structure. Mol Cell 3, 661-671.

Peters-Golden, M. & Henderson Jr., W. R. (2007). Leukotrienes. N. Eng. J. Med. 357, 1841-1854.

Powell W. S., and Rokach J. (2005) Biochemistry, biology and chemistry of the 5-lipoxygenase product 5-oxo-ETE. Prog Lipid Res. 44, 154-183.

Remington, J. P. (1991) Remington's Pharmaceutical Sciences. Mack Pub. Co.

Roversi, P. R., Lissina, O., Johnson, S., Ahmat, N., Paesen, G. C., Ploss, K., Boland, W., Nunn, M. A., and Lea, S. R. (2007) The structure of OmCl a novel lipocalin inhibitor of the complement system. J. Mol. Biol. 369:784-93.

Roversi, P., Ryffel, B., Togbe, D., Maillet, I., Teixeira, M., Ahmat, N., Paesen, G., Lissina, O., Boland, W., Ploss, K., Caesar, J., Leonhartsberger, S., Lea, S., and Nunn, M. (2013) Bifunctional Lipocalin Ameliorates Murine Immune Complex-induced Acute Lung Injury. J. Biol. Chem 288: 18789-18802

Sambrook, J., Fritsch, E. F., Maniatis, T. (1989) Molecular Cloning: A Laboratory Manual Samuelsson, B. (1983). Leukotrienes: mediators of immediate hypersensitivity reactions and inflammation. Science 220, 569-575.

Schlapschy, M., Binder, U., Börger, C., Theobald, I., Wachinger, K., Kisling, S., Haller, D., Skerra, A. (2013) PASylation: a biological alternative to PEGylation for extending the plasma half-life of pharmaceutically active proteins. Protein Eng Des Sel 26: 489-501

Schwartz, G. K., Weitzman, A., O'Reilly, E., Brail, L., de Alwis, D. P., Cleverly, A., Barile-Thiem, B., Vinciguerra, V., and Budman D. R. (2005) Phase I and Pharmacokinetic Study of LY293111, an Orally Bioavailable LTB4 Receptor Antagonist, in Patients With Advanced Solid Tumors. Journal of Clinical Oncology, 23, 5365-5373.

Sebaldt, R. J., Sheller, J. R., Oates, J. A., Roberts, L. J. and FitzGerald G. A. (1990). Inhibition of eicosanoid biosynthesis by glucocorticoids in humans. Proc Natl Acad Sd. U.S.A. 8, 6974-6978.

Shao W. H., Del Prete A., Bock C. B., Haribabu B. (2006) Targeted Disruption of Leukotriene B4 Receptors BLTI and BLT2: A Critical Role for BLTI in Collagen-Induced Arthritis in Mice. J. Immunol. 176, 6254-6261.

Sharma, J. N. and Mohammed, L. A. (2006). The role of leukotrienes in the pathophysiology of inflammatory disorders: is there a case for revisiting leukotrienes as therapeutic targets? Immunopharmacology 14, 10-16.

Showell, H. J., Pettipher, E. R., Cheng, J. B., Breslow, R., Conklyn, M., Farrell, C A, Hingorani, G. P., Salter, E. D., Hackman, B. C., Wimberly, D J. et al (1995). The in vitro and in vivo pharmacologic activity of the potent and selective leukotriene B4 receptor antagonist CP-105696. J. Pharm. Exp. Ther. 273, 176-184.

Sitaru, C., et al. Induction of dermal-epidermal separation in mice by passive transfer of antibodies specific to type VII collagen J Clin Invest 2005; 115:870-8.

Spector, D. L., Goldman, R. D., Leinwand, L. A. (1998) Cells: a laboratory manual. Cold Spring Harbor Laboratory Press.

Tager, A. M. and Luster, A. D. (2003). BLTI and BLT2: the leukotriene B(4) receptors. Prostaglandins Leukot. Essent. Fatty Acids 69, 123-134.

Taube C, Miyahara N., Ott V., Swanson B., Takeda K., Loader J., Shultz L. D., Tager A. M., Luster A. D., Dakhama A., and Gelfand E. W. (2006) The leukotriene B4 receptor BLTI is required for effector CD8+ T cell-mediated, mast cell-dependent airway hyperresponsiveness. J. Immunol. 176, 3157-3164.

Yamaoka, K A., Claesson, H. E., and Rosen, A. (1989) Leukotriene B4 enhances activation, proliferation, and differentiation of human B lymphocytes. J. Immunol. 143, 1996-2000.

Yokomizo, T., Kato, K., Higiya, H., Izumi, T. and Shimizu, T. (1997). A G-protein coupled receptor for leukotriene B4 that mediates chemotaxis. Nature 387, 620-624.

Yokomizo, T., Kato, K., Terwaki, K., Y., Izumi, T. and Shimizu, T. (2000). A second leukotriene B(4) receptor, BLT2. A new therapeutic target in inflammation and immunological disorders. J. Exp. Med. 192, 421-432.

Yokomizo, T., Isumi, T., Chang, K., Takuwa, Y., Shimizu, T. (2001). Hydroxyeicosanoids bind to and activate the low affinity leukotriene B4 receptor BLT2. J. Biol. Chem. 276, 12454-12459.

The invention claimed is:

1. A modified Coversin polypeptide which exhibits leukotriene or hydroxyeicosanoid binding activity, said modified Coversin polypeptide comprising SEQ ID NO: 3 in which from 1 to 30 amino acid substitutions are made, wherein (i) in positions 114 to 124 of SEQ ID NO: 3 one or more of the following substitutions (a)-(j) is made:

a. Met114 is replaced with Gln, Asp, Asn, Glu, Arg, Lys, Gly, Ala, Pro, His, or Thr;

b. Met116 is replaced with Gln, Asp, Asn, Glu, Arg, Lys, Gly, Ala, Pro, His, or Thr;

c. Leu117 is replaced with Ser, Asp, Asn, Glu, Arg, Lys, Gly, Ala, or Pro;

d. Asp118 is replaced with Asn, Gln, Arg, Lys, Gly, Ala, Leu, Ser, Ile, Phe, Tyr, Met Pro, His, or Thr;

e. Ala119 is replaced with Gly, Asp, Asn, Glu, Arg, Lys, Leu, Ile, Phe, Tyr, Met, Pro, or His;

f Gly120 is replaced with Ser, Asp, Asn, Glu, Arg, Lys, Leu, Ile, Phe, Tyr, Met, Pro, or His;

g. Gly121 is replaced with Ala, Asp, Asn, Glu, Arg, Lys, Leu, Ile, Phe, Tyr, Met, Pro, or His;

h. Leu122 is replaced with Asp, Glu, Asn, Ala, Gln, Arg, Lys, Pro, or His;

i. Glu123 is replaced with Asp, Ala, Gln, Asn, Arg, Lys, Gly, Leu, Ser, Ile, Phe, Tyr, Pro, His, or Thr;

j. Val124 is replaced with Lys, Gln, Asn, Arg, Lys, Gly, Ala, Pro, His, or Thr; and wherein (ii) Ala44 in SEQ ID NO: 3 is replaced with Asn, Asp, Gln, Glu, Arg, Lys, Leu, Ile, Phe, Tyr, Met, Pro, or His;

or a fragment thereof in which up to five amino acids are deleted from the N terminus of the modified Coversin polypeptide.

2. A modified Coversin polypeptide according to claim 1 wherein in positions 114 to 124 of SEQ ID NO: 3 one or more of the following substitutions (a)-(j) is made:

a. Met114 is replaced with Gln;

b. Met116 is replaced with Gln;

c. Leu117 is replaced with Ser;

d. Asp118 is replaced with Asn;

e. Ala119 is replaced with Gly;

f Gly120 is replaced with Ser;

g. Gly121 is replaced with Ala;

h. Leu122 is replaced with Asp;

i. Glu123 is replaced with Asp, or Ala;

j. Val124 is replaced with Lys; and wherein (i) Ala44 in SEQ ID NO: 3 is replaced with Asn44;

or a fragment thereof in which up to five amino acids are deleted from the N terminus of the modified Coversin polypeptide.

3. A modified Coversin polypeptide or fragment thereof according to claim 1, wherein two or more of the substitutions (a)-(j) are present.

4. A modified Coversin polypeptide or fragment thereof according to claim 3, wherein five or more of the substitutions (a)-(j) are present.

5. A modified Coversin polypeptide or fragment thereof according to claim 4, wherein each of the substitutions (a)-(j) is present, optionally wherein Trp 115 is not substituted.

6. A modified Coversin polypeptide or fragment thereof according to claim 4, wherein each of the substitutions (a)-(j) as defined in claim 2 is present, optionally wherein Trp 115 is not substituted.

7. The modified polypeptide or fragment thereof according to claim 6, wherein Glu123 is replaced with Asp.

8. A modified Coversin polypeptide or fragment thereof according to claim 1, which has a loop sequence between amino acid positions 114 to 124 of SEQ ID NO:3 as set out in SEQ ID NO:10 and which has 1-15 additional substitutions compared to SEQ ID NO:3 beyond those that are set out in SEQ ID NO:5.

9. The modified Coversin polypeptide or fragment thereof according to claim 8, which has 2-10 additional substitutions compared to SEQ ID NO:3 beyond those that are set out in SEQ ID NO:5.

10. The modified Coversin polypeptide or fragment thereof according to claim 8, which has 3-5 additional substitutions compared to SEQ ID NO:3 beyond those that are set out in SEQ ID NO:5.

11. The modified Coversin polypeptide or fragment thereof according to claim 1 which consists of or comprises SEQ ID NO:5.

12. A modified Coversin polypeptide or fragment thereof according to claim 1, wherein:

a. Met116 is replaced with Gln, Asp, Asn, Glu, Arg, Lys, Gly, Ala, Pro, His, or Thr, preferably Gln;

b. Leu117 is replaced with Ser, Asp, Asn, Glu, Arg, Lys, Gly, Ala, or Pro, preferably Ser;

c. Gly121 is replaced with Ala, Asp, Asn, Glu, Arg, Lys, Leu, Ile, Phe, Tyr, Met, Pro, or His, preferably Ala;

d. Leu122 is replaced with Asp, Glu, Asn, Ala, Gln, Arg, Lys, Pro, or His, preferably Asp; and e. Glu123 is replaced with Asp, Ala, Gln, Asn, Arg, Lys, Gly, Leu, Ser, Ile, Phe, Tyr, Pro, His, or Thr, preferably Ala or Asp.

13. A modified Coversin polypeptide or fragment thereof according to claim 12, wherein in positions 114 to 124 of SEQ ID NO: 3:

a. Met116 is replaced with Gln;

b. Leu117 is replaced with Ser;

c. Gly121 is replaced with Ala;

d. Leu122 is replaced with Asp; and e. Glu123 is replaced with Ala.

14. A modified Coversin polypeptide or fragment thereof according to claim 12, wherein Trp 115 is not substituted.

15. A modified Coversin polypeptide or fragment thereof according to claim 12, wherein Met114, Trp 115, Asp118, Ala119, Gly120 and Val124 are not substituted.

16. A modified Coversin polypeptide or fragment thereof according to claim 1, which has a loop sequence between amino acid positions 114 to 124 of SEQ ID NO:3 as set out in SEQ ID NO:11 and which has 1-20 additional substitutions compared to SEQ ID NO:3 beyond those that are set out in SEQ ID NO:6.

17. The modified Coversin polypeptide or fragment thereof according to claim 16, which has 2-15 additional substitutions compared to SEQ ID NO:3 beyond those that are set out in SEQ ID NO:6.

18. The modified Coversin polypeptide or fragment thereof according to claim 16, which has 3-10 additional substitutions compared to SEQ ID NO:3 beyond those that are set out in SEQ ID NO:6.

19. A modified Coversin polypeptide or fragment thereof according to claim 1, wherein:

a. Met116 is replaced with Gln, Asp, Asn, Glu, Arg, Lys, Gly, Ala, Pro, His, or Thr;

b. Leu122 is replaced with Asp, Glu, Asn, Ala, Gln, Arg, Lys, Pro, or His.

20. A modified Coversin polypeptide or fragment thereof according to claim 19, wherein a. Met116 is replaced with Gln; and b. Leu122 is replaced with Asp.

21. A modified Coversin polypeptide or fragment thereof according to claim 20, wherein Trp 115 is not substituted.

22. A modified Coversin polypeptide or fragment thereof according to claim 20, wherein Met114, Trp 115, Leu117, Asp118, Ala119, Gly120, Gly121, Glu123 and Val124 are not substituted.

23. A modified Coversin polypeptide or fragment thereof according to claim 1, which has a loop sequence between amino acid positions 114 to 124 of SEQ ID NO:3 as set out in SEQ ID NO:12 and which has 1-25 additional substitutions compared to SEQ ID NO:3 beyond those that are set out in SEQ ID NO:7.

24. The modified Coversin polypeptide or fragment thereof according to claim 23, which has 2-12 additional substitutions compared to SEQ ID NO:3 beyond those that are set out in SEQ ID NO:7.

25. The modified Coversin polypeptide or fragment thereof according to claim 24, which has 3-15 additional substitutions compared to SEQ ID NO:3 beyond those that are set out in SEQ ID NO:7.

26. The modified Coversin polypeptide according to claim 1, which consists of or comprises SEQ ID NO:7.

27. A modified Coversin polypeptide or fragment thereof according to claim 1, wherein Ala44 in SEQ ID NO: 3 is replaced with Asn.

28. A modified Coversin polypeptide or fragment thereof according to claim 1, wherein Asp149 in SEQ ID NO: 3 is replaced with Gly, Gln, Asn, Ala, Met, Arg, Lys, Leu, Ser, Ile, Phe, Tyr, Pro, His, or Thr.

29. A modified Coversin polypeptide or fragment thereof according to claim 28, wherein Ala44 in SEQ ID NO: 3 is replaced with Asn and Asp149 in SEQ ID NO: 3 is replaced with Gly.

30. A modified Coversin polypeptide or fragment thereof according to claim 1, wherein the six cysteine amino acids at positions 6, 38, 100, 128, 129, 150 of SEQ ID NO: 3 are retained in unmodified form.

31. A modified Coversin polypeptide or fragment thereof according to claim 1, wherein Asn60 and Asn84 are each replaced with Gln.

32. A modified Coversin polypeptide or fragment thereof according to claim 1, wherein one or more of the following amino acids is not substituted: Phe18, Tyr25, Arg36, Leu39, Gly41, Pro43, Leu52, Val54, Met56, Phe58, Thr67, Trp69, Phe71, Gln87, Arg89, His99, His101, Asp103, and Trp115.

33. A modified Coversin polypeptide or fragment thereof according to claim 32, wherein all of the following amino acids are not substituted: Phe18, Tyr25, Arg36, Leu39, Gly41, Pro43, Leu52, Val54, Met56, Phe58, Thr67, Trp69, Phe71, Gln87, Arg89, His99, His101, Asp103, and Trp115.

34. A modified Coversin polypeptide or fragment thereof according to claim 1, wherein:

a. none of amino acids 5, 6, 11, 13-15, 20-21, 24-27, 29-32, 35-41, 45, 47-48, 50, 52-60, 64, 66, 69-81, 83, 84, 86, 90-94, 97-104, 112-113, 115, 125-129, 132-139, 145, 148, and 150 in SEQ ID NO:3 are substituted; or b. none of amino acids 5, 6, 11, 13-15, 18, 20-21, 24-27, 29-32, 35-41, 43, 45, 47-48, 50, 52-60, 64, 66, 67, 69-81, 83, 84, 86, 87, 89, 90-94, 97-104, 112-113, 115, 125-129, 132-139, 145, 148, and 150 in SEQ ID NO:3 are substituted; or c. none of amino acids 5, 6, 11, 13-15, 18, 20-21, 24-25, 27, 30-32, 35-41, 43, 47-48, 50, 52-60, 64, 66, 67, 69-81, 83, 84, 86, 87, 89, 90-94, 98, 100, 102-104, 112-113, 115, 126, 128-129, 132-139, 145, 148, and 150 in SEQ ID NO:3 are substituted.

35. A modified Coversin polypeptide according to claim 1, which comprises or consists of the sequence SEQ ID NO: 8.

36. A modified Coversin polypeptide or fragment thereof according to claim 1 or a fragment thereof which binds to LTB4.

37. A fusion protein comprising a modified Coversin polypeptide according to claim 1 that is genetically or chemically fused to one or more peptides or polypeptides.

38. The fusion protein of claim 37 which comprises a PAS sequence.

39. The fusion protein of claim 38 which comprises a PAS sequence consisting of 30 copies of SEQ ID NO:13, fused to the N terminus of the modified Coversin polypeptide.

40. The fusion protein of claim 38 wherein said fusion protein comprises (a) a PAS sequence consisting of 30 copies of SEQ ID NO:13 and (b) (i) amino acids 19-168 of SEQ ID NO:2, wherein (a) is fused to the N terminus of (b).

41. A composition comprising a modified Coversin polypeptide according to claim 1 in conjunction with a pharmaceutically acceptable carrier.

42. The modified Coversin polypeptide or fragment thereof according to claim 12, wherein Asp149 in SEQ ID NO: 3 is replaced with Gly, Gln, Asn, Ala, Met, Arg, Lys, Leu, Ser, Ile, Phe, Tyr, Pro, His, or Thr.

43. The modified Coversin polypeptide of fragment thereof according to claim 42, wherein Met114, Trp115, Asp118, Ala119, Gly120 and Val124 are not substituted.

44. The modified Coversin polypeptide or fragment thereof according to claim 1 which consists of or comprises SEQ ID NO: 6.

45. A nucleic acid molecule encoding a modified Coversin polypeptide or a fragment thereof in which up to five amino acids are deleted from the N terminus of the modified Coversin polypeptide or a fusion protein comprising the modified Coversin polypeptide that is genetically or chemically fused to one or more peptides or polypeptides, wherein the modified Coversin polypeptide comprises SEQ ID NO: 3 in which from 1 to 30 amino acid substitutions are made, wherein (i) in positions 114 to 124 of SEQ ID NO: 3 one or more of the following substitutions (a)-(j) is made:

a. Met114 is replaced with Gln, Asp, Asn, Glu, Arg, Lys, Gly, Ala, Pro, His, or Thr;

b. Met116 is replaced with Gln, Asp, Asn, Glu, Arg, Lys, Gly, Ala, Pro, His, or Thr;

c. Leu117 is replaced with Ser, Asp, Asn, Glu, Arg, Lys, Gly, Ala, or Pro;

d. Asp118 is replaced with Asn, Gln, Arg, Lys, Gly, Ala, Leu, Ser, Ile, Phe, Tyr, Met Pro, His, or Thr;

e. Ala119 is replaced with Gly, Asp, Asn, Glu, Arg, Lys, Leu, Ile, Phe, Tyr, Met, Pro, or His;

f Gly120 is replaced with Ser, Asp, Asn, Glu, Arg, Lys, Leu, Ile, Phe, Tyr, Met, Pro, or His;

g. Gly121 is replaced with Ala, Asp, Asn, Glu, Arg, Lys, Leu, Ile, Phe, Tyr, Met, Pro, or His;

h. Leu122 is replaced with Asp, Glu, Asn, Ala, Gln, Arg, Lys, Pro, or His;

i. Glu123 is replaced with Asp, Ala, Gln, Asn, Arg, Lys, Gly, Leu, Ser, Ile, Phe, Tyr, Pro, His, or Thr;

j. Val124 is replaced with Lys, Gln, Asn, Arg, Lys, Gly, Ala, Pro, His, or Thr; and wherein (ii) Ala44 in SEQ ID NO: 3 is replaced with Asn, Asp, Gln, Glu, Arg, Lys, Leu, Ile, Phe, Tyr, Met, Pro, or His.

46. A vector comprising a nucleic acid molecule according to claim 45.

47. A host cell comprising a nucleic acid molecule according to claim 45 or a vector comprising the nucleic acid molecule.

48. A method for preparing a modified Coversin polypeptide or a fragment thereof according to claim 1 or a fusion protein comprising the modified Coversin polypeptide according to claim 1 that is genetically or chemically fused to one or more peptides or polypeptides comprising culturing a host cell comprising a nucleic acid molecule encoding the modified Coversin polypeptide or fragment thereof or encoding the fusion protein under conditions whereby said modified Coversin polypeptide or fragment thereof or the fusion protein is expressed and recovering said protein thus produced.

* * * * *

UNITED STATES PATENT AND TRADEMARK OFFICE
CERTIFICATE OF CORRECTION

PATENT NO. : 11,214,602 B2
APPLICATION NO. : 16/603357
DATED : January 4, 2022
INVENTOR(S) : Miles Nunn It is certified that error appears in the above-identified patent and that said Letters Patent is hereby corrected as shown below:

In the Claims

In Column 41, Line 42, please change "f Gly120" to --f. Gly120--.
In Column 46, Line 1, please change "f Gly120" to --f. Gly120--.

Signed and Sealed this
Twenty-fourth Day of May, 2022

Katherine Kelly Vidal

Katherine Kelly Vidal
*Director of the United States Patent and Trademark Office*

SEQUENCE LISTING

```
<160> NUMBER OF SEQ ID NOS: 19

<210> SEQ ID NO 1
<211> LENGTH: 507
<212> TYPE: DNA
<213> ORGANISM: Ornithodoros moubata

<400> SEQUENCE: 1

atgctggttt tggtgaccct gattttctcc ttttctgcga acatcgcata tgctgacagc     60

gaaagcgact gcactggaag cgaacctgtt gacgccttcc aagctttcag tgagggcaaa    120

gaggcatatg tcctggtgag gtccacggat cccaaagcga gggactgctt gaaaggagaa    180

ccagccggag aaaagcagga caacacgttg ccggtgatga tgacgtttaa gaatggcaca    240

gactgggctt caaccgattg gacgtttact ttggacggcg caaaggtaac ggcaaccctt    300

ggtaacctaa cccaaaatag ggaagtggtc tacgactcgc aaagtcatca ctgccacgtt    360

gacaaggtcg agaaggaagt tccagattat gagatgtgga tgctcgatgc gggagggctt    420

gaagtggaag tcgagtgctg ccgtcaaaag cttgaagagt tggcgtctgg caggaaccaa    480

atgtatcccc atctcaagga ctgctag                                        507


<210> SEQ ID NO 2
<211> LENGTH: 168
<212> TYPE: PRT
<213> ORGANISM: Ornithodoros moubata

<400> SEQUENCE: 2
```

-continued

```
Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys
                165


<210> SEQ ID NO 3
<211> LENGTH: 150
<212> TYPE: PRT
<213> ORGANISM: Ornithodoros moubata

<400> SEQUENCE: 3

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Ala Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Met Leu Asp Ala Gly Gly Leu Glu Val Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Asp Cys
145                 150


<210> SEQ ID NO 4
<211> LENGTH: 453
<212> TYPE: DNA
<213> ORGANISM: Ornithodoros moubata

<400> SEQUENCE: 4
```

```
gacagcgaaa gcgactgcac tggaagcgaa cctgttgacg ccttccaagc tttcagtgag      60

ggcaaagagg catatgtcct ggtgaggtcc acggatccca aagcgaggga ctgcttgaaa     120

ggagaaccag ccggagaaaa gcaggacaac acgttgccgg tgatgatgac gtttaagaat     180

ggcacagact gggcttcaac cgattggacg tttactttgg acggcgcaaa ggtaacggca     240

acccttggta acctaaccca aaatagggaa gtggtctacg actcgcaaag tcatcactgc     300

cacgttgaca aggtcgagaa ggaagttcca gattatgaga tgtggatgct cgatgcggga     360

gggcttgaag tggaagtcga gtgctgccgt caaaagcttg aagagttggc gtctggcagg     420

aaccaaatgt atccccatct caaggactgc tag                                  453


<210> SEQ ID NO 5
<211> LENGTH: 150
<212> TYPE: PRT
<213> ORGANISM: Artificial Sequence
<220> FEATURE:
<223> OTHER INFORMATION: Synthetic peptide

<400> SEQUENCE: 5

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Ala Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Gln Trp Gln Ser Asn Gly Ser Ala Asp Asp Lys Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Asp Cys
145                 150


<210> SEQ ID NO 6
<211> LENGTH: 150
<212> TYPE: PRT
<213> ORGANISM: Artificial Sequence
<220> FEATURE:
<223> OTHER INFORMATION: Synthetic peptide

<400> SEQUENCE: 6

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Asn Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
```

```
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Gln Ser Asp Ala Gly Ala Asp Ala Val Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Gly Cys
145                 150


<210> SEQ ID NO 7
<211> LENGTH: 150
<212> TYPE: PRT
<213> ORGANISM: Artificial Sequence
<220> FEATURE:
<223> OTHER INFORMATION: Synthetic peptide

<400> SEQUENCE: 7

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Asn Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Gln Leu Asp Ala Gly Gly Asp Glu Val Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Gly Cys
145                 150


<210> SEQ ID NO 8
<211> LENGTH: 150
<212> TYPE: PRT
<213> ORGANISM: Artificial Sequence
<220> FEATURE:
<223> OTHER INFORMATION: Synthetic peptide

<400> SEQUENCE: 8

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Asn Gly Glu Lys Gln
        35                  40                  45

Asp Asn Thr Leu Pro Val Met Met Thr Phe Lys Asn Gly Thr Asp Trp
    50                  55                  60
```

```
Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Met Leu Asp Ala Gly Gly Leu Glu Val Glu Val Glu Cys
        115                 120                 125

Cys Arg Gln Lys Leu Glu Glu Leu Ala Ser Gly Arg Asn Gln Met Tyr
    130                 135                 140

Pro His Leu Lys Asp Cys
145                 150
```

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

```
Met Trp Met Leu Asp Ala Gly Gly Leu Glu Val
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

```
Gln Trp Gln Ser Asn Gly Ser Ala Asp Asp Lys
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

```
Met Trp Gln Ser Asp Ala Gly Ala Asp Ala Val
1               5                   10
```

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

```
Met Trp Gln Leu Asp Ala Gly Gly Asp Glu Val
1               5                   10
```

<210> SEQ ID NO 13
<211> LENGTH: 20
<212> TYPE: PRT
<213> ORGANISM: Artificial Sequence
<220> FEATURE:
<223> OTHER INFORMATION: PAS sequence

<400> SEQUENCE: 13

```
Ala Ser Pro Ala Ala Pro Ala Pro Ala Ser Pro Ala Ala Pro Ala Pro
1               5                   10                  15

Ser Ala Pro Ala
            20


<210> SEQ ID NO 14
<211> LENGTH: 20
<212> TYPE: PRT
<213> ORGANISM: Artificial Sequence
<220> FEATURE:
<223> OTHER INFORMATION: PAS sequence

<400> SEQUENCE: 14

Ala Ala Pro Ala Ser Pro Ala Pro Ala Ala Pro Ser Ala Pro Ala Pro
1               5                   10                  15

Ala Ala Pro Ser
            20


<210> SEQ ID NO 15
<211> LENGTH: 20
<212> TYPE: PRT
<213> ORGANISM: Artificial Sequence
<220> FEATURE:
<223> OTHER INFORMATION: PAS sequence

<400> SEQUENCE: 15

Ala Pro Ser Ser Pro Ser Pro Ser Ala Pro Ser Ser Pro Ser Pro Ala
1               5                   10                  15

Ser Pro Ser Ser
            20


<210> SEQ ID NO 16
<211> LENGTH: 20
<212> TYPE: PRT
<213> ORGANISM: Artificial Sequence
<220> FEATURE:
<223> OTHER INFORMATION: PAS sequence

<400> SEQUENCE: 16

Ser Ala Pro Ser Ser Pro Ser Pro Ser Ala Pro Ser Ser Pro Ser Pro
1               5                   10                  15

Ala Ser Pro Ser
            20


<210> SEQ ID NO 17
<211> LENGTH: 20
<212> TYPE: PRT
<213> ORGANISM: Artificial Sequence
<220> FEATURE:
<223> OTHER INFORMATION: PAS sequence

<400> SEQUENCE: 17

Ser Ser Pro Ser Ala Pro Ser Pro Ser Ser Pro Ala Ser Pro Ser Pro
1               5                   10                  15

Ser Ser Pro Ala
            20


<210> SEQ ID NO 18
<211> LENGTH: 24
<212> TYPE: PRT
<213> ORGANISM: Artificial Sequence
<220> FEATURE:
<223> OTHER INFORMATION: PAS sequence
```

-continued

```
<400> SEQUENCE: 18

Ala Ala Ser Pro Ala Ala Pro Ser Ala Pro Pro Ala Ala Ala Ser Pro
1               5                   10                  15

Ala Ala Pro Ser Ala Pro Pro Ala
            20


<210> SEQ ID NO 19
<211> LENGTH: 20
<212> TYPE: PRT
<213> ORGANISM: Artificial Sequence
<220> FEATURE:
<223> OTHER INFORMATION: PAS sequence

<400> SEQUENCE: 19

Ala Ser Ala Ala Ala Pro Ala Ala Ala Ser Ala Ala Ala Ser Ala Pro
1               5                   10                  15

Ser Ala Ala Ala
            20
```